US006485849B2

(12) United States Patent
Petticrew

(10) Patent No.: US 6,485,849 B2
(45) Date of Patent: *Nov. 26, 2002

(54) METHOD FOR MOLDING DENTAL RESTORATIONS AND RELATED APPARATUS

(75) Inventor: Richard W. Petticrew, Odessa, FL (US)

(73) Assignee: Tec Ventures, Inc., Odessa, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/779,465

(22) Filed: Feb. 9, 2001

(65) Prior Publication Data

US 2001/0031446 A1 Oct. 18, 2001

Related U.S. Application Data

(63) Continuation-in-part of application No. 09/695,189, filed on Oct. 24, 2000, which is a continuation-in-part of application No. 09/235,171, filed on Jan. 22, 1999, now Pat. No. 6,346,306, which is a division of application No. 08/927,774, filed on Sep. 11, 1997, now Pat. No. 5,897,885, which is a division of application No. 08/417,682, filed on Apr. 6, 1995, now Pat. No. 5,702,514, which is a continuation-in-part of application No. 08/250,926, filed on May 31, 1994, now Pat. No. 5,507,981.
(60) Provisional application No. 60/184,741, filed on Feb. 24, 2000.

(51) Int. Cl.$^7$ .................... C03C 10/06; A61C 13/08; B32B 9/00
(52) U.S. Cl. .................. 428/697; 428/689; 428/699; 428/701; 428/702; 501/5; 433/201.1; 433/202.1; 433/212.1; 106/35
(58) Field of Search .................. 428/689, 697, 428/699, 701, 702; 501/20, 2, 4, 7, 63, 66, 68, 77, 5; 433/199.1, 201.1, 212.1, 202.1; 106/35

(56) References Cited

U.S. PATENT DOCUMENTS

| | | | | |
|---|---|---|---|---|
| 4,189,325 A | * | 2/1980 | Barrett et al. | 106/35 |
| 5,106,303 A | * | 4/1992 | Oden et al. | 433/223 |
| 5,176,961 A | * | 1/1993 | Crooker et al. | 428/409 |
| 5,219,799 A | * | 6/1993 | Beall et al. | 501/5 |
| 5,618,763 A | * | 4/1997 | Frank et al. | 501/5 |
| 5,653,791 A | * | 8/1997 | Panzera et al. | 501/57 |
| 5,702,514 A | * | 12/1997 | Petticrew | 106/35 |
| 6,376,397 B1 | * | 4/2002 | Petticrew | 501/5 |

OTHER PUBLICATIONS

Page Glass Engineering Handbook 3rd Ed by Mc Lellan & Errol B. Shand No date.
Page Modern Glass Pratice 1952 by Samuel R Scholes No month.
Page Silicate Glass Technology Methods 1977 by Clarence L Babcock No month.

* cited by examiner

Primary Examiner—Deborah Jones
Assistant Examiner—Stephen Stein
(74) Attorney, Agent, or Firm—Donald R. Bahr

(57) ABSTRACT

The present invention is concerned with a process for the formation of dental restorations from glass-ceramic materials and the resulting dental restorations. A dental restoration is prepared by placing a glass-ceramic material in a heat-pressure deformable crucible. Heat is applied to the crucible to bring the glass-ceramic to a working range at temperatures above its liquidus temperature. The crucible has heat-pressure deformation properties which are matched to the working temperature of the glass-ceramic. Once the glass-ceramic is heated to its working temperature, the crucible is brought into contract with a mold having a cavity therein. As the distance between the heated crucible and the mold is decreased, the crucible is deformed to form a seal with the mold facilitating the injection of the molten glass-ceramic into the cavity. The resulting dental restoration has superior optical, esthetic and strength properties.

14 Claims, 5 Drawing Sheets

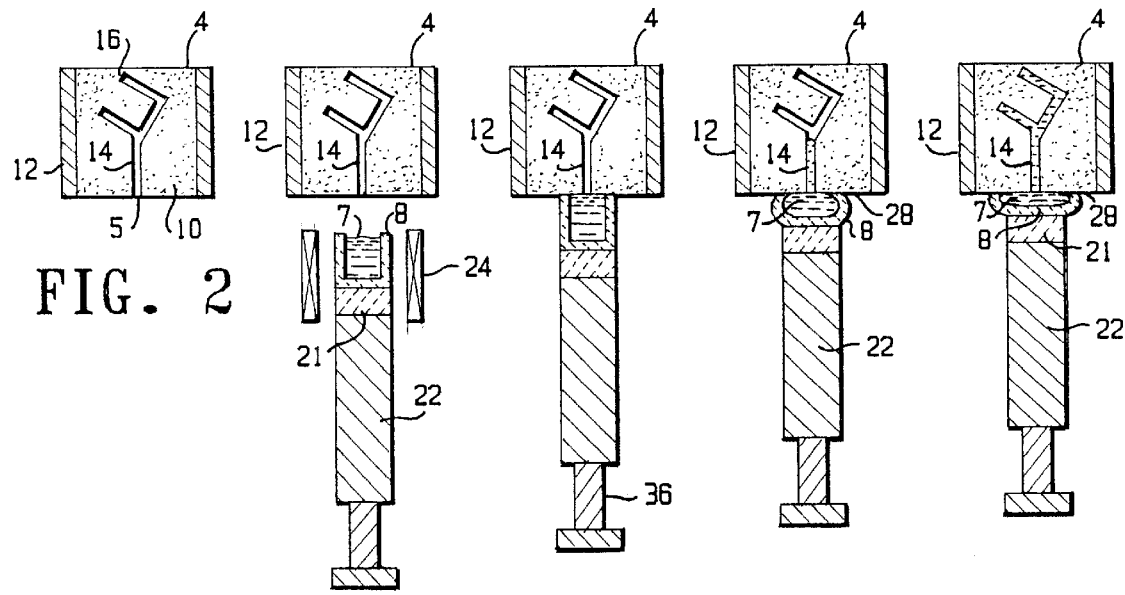
FIG. 2    FIG. 3  FIG. 4  FIG. 5  FIG. 6
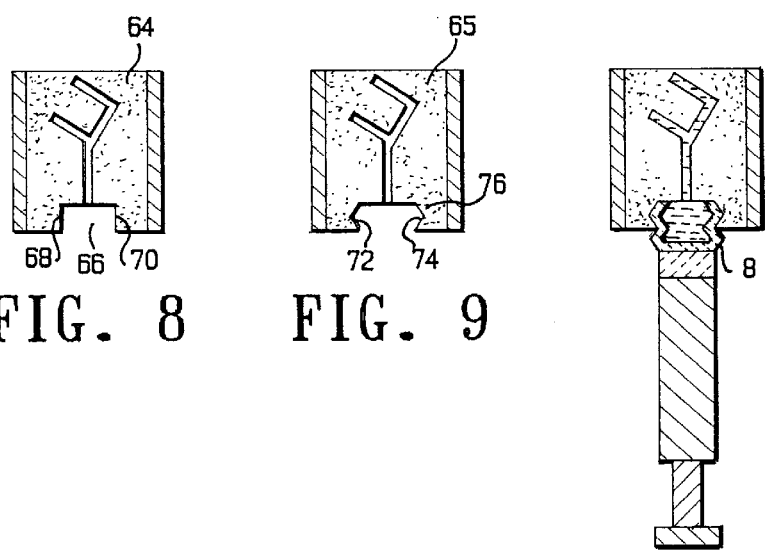
FIG. 8    FIG. 9
FIG. 10

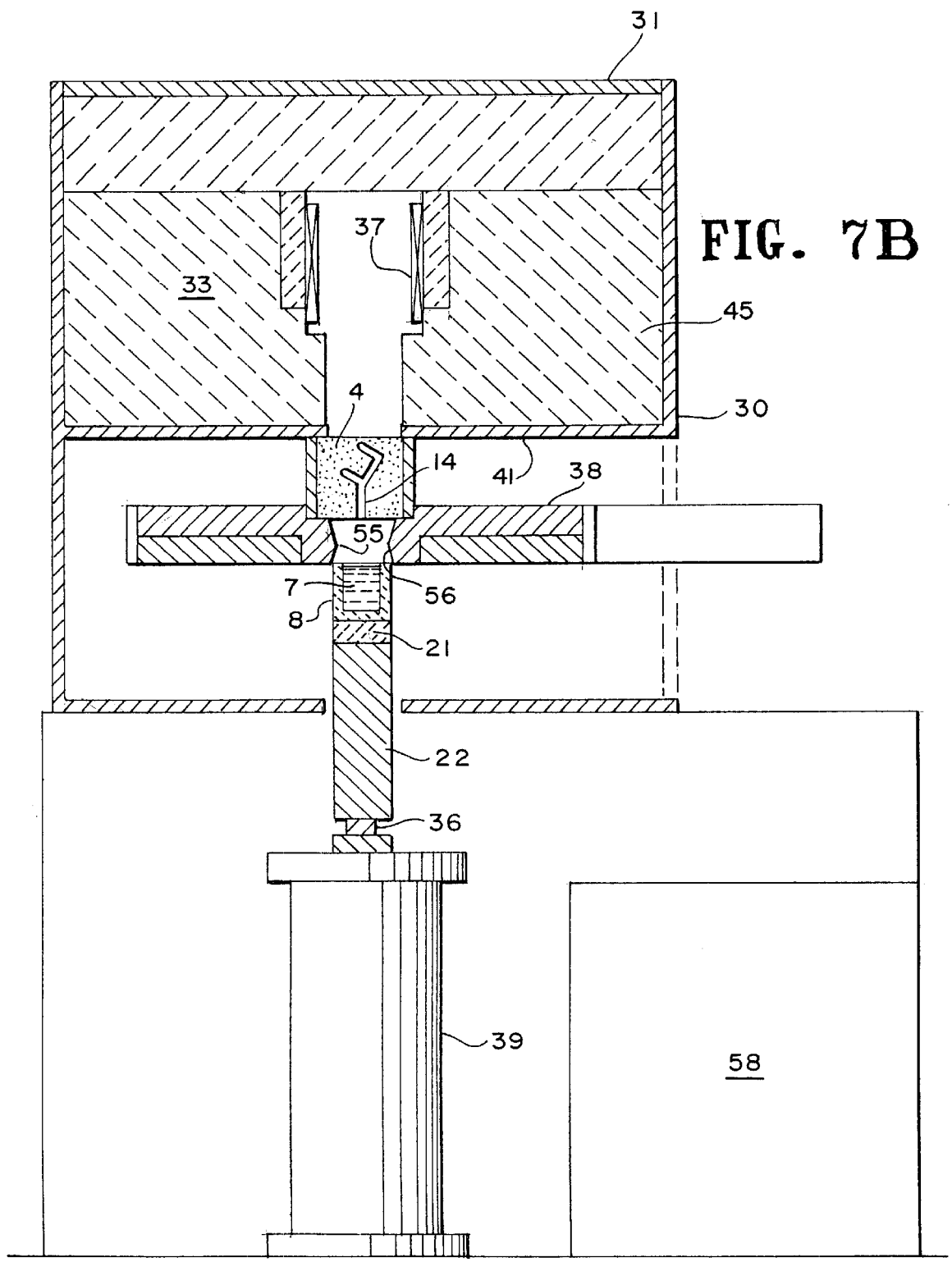

METHOD FOR MOLDING DENTAL RESTORATIONS AND RELATED APPARATUS

RELATED APPLICATIONS

This application is a continuation-in-part application of application Ser. No. 09/695,189, filed Oct. 24, 2000, which is a continuation in part of application Ser. No. 09/235,171, filed Jan. 22, 1999, now U.S. Pat. No. 6,346,306 which is a divisional application of Ser. No. 08/927,774, filed Sep. 11, 1997, U.S. Pat. No. 5,897,885, which is a divisional application of Ser. No. 08/417,682, filed Apr. 6, 1995, U.S. Pat. No. 5,702,514, which is a continuation-in-part of application Ser. No. 08/250,926, filed May 31, 1994, U.S. Pat. No. 5,507,981.

This application claims priority of provisional application Ser. No. 60/184,741 Filed Feb. 24, 2000.

FIELD OF THE INVENTION

The present invention relates to a process for the molding of metal free dental restorations such as crowns, bridges, inlays, onlays, etc., from glass-ceramic materials. The invention is also concerned with apparatus which permits dental restorations to be easily molded from glass-ceramic materials and, lastly, the invention relates to the resulting dental restorations.

BACKGROUND OF THE INVENTION

In the prior art, various methods have been used to form metal free dental restorations from glass-ceramic materials. Glass ceramic materials because of their strength, translucency, non-toxicity and other physical properties are ideal materials for use in forming dental restorations. Because of their suitability, glass-ceramic materials have been used to form dental restorations for at least eighty years. In the prior art, the most widely used means for forming dental restorations from mixtures of glass and ceramic materials is a process which utilized a slurry of glass and ceramic particles. In this process, a die is formed which is an exact replica of the remaining portion of the tooth to which the restoration is to be secured. It is understood by one skilled in the art that the remaining portion of the tooth has been prepared by the dentist in such a manner that the attachment of the restoration is facilitated. To start the process, the dentist takes an impression of the prepared tooth to create a negative impression of the prepared tooth or teeth. This negative impression is then packed with a material to form a positive impression of the prepared tooth or teeth. This positive impression is called a die. Platinum foil is then pressed over the die to form a matrix which is essentially a foundation on which the dental restoration is built. In order to form up the dental restoration, many layers of a slurry of a particulate glass-ceramic material are applied to the platinum foil matrix. As multiple layers of the slurry are built-up and dried, a semi-solid structure is formed which can be carved into shape of the desired dental restoration. Once the desired shape is achieved, the structure is then removed from the die. At this stage, the structure is referred to as a green structure. The structure is then fired. During the firing process, the particulate glass-ceramic material fuses into a solid mass. Because the green structure is formed from multiple layers of the dried glass-ceramic material, uneven fusing may result. As a result of this uneven fusing, the physical properties of the finished restoration may be detrimentally affected, thereby creating an inferior dental restoration. Further, as can be seen from the above description, the overall process is very labor intensive.

Other methods for forming the green restoration have been considered in the prior art, for example, in U.S. Pat. No. 2,196,258, a mixture of particulate glass and ceramic materials which incorporates a binder is packed into a flexible mold to form a green structure which is then fired to form a finished structure. Again, because the process entails the fusing of particulate material, uneven fusing may result and, hence, a weakened and inferior dental restoration may result.

To overcome the problems as described above, the trade has recognized that in order to produce strong, translucent metal free dental restorations, it would be desirable to form these restorations directly from a homogenous, molten glass-ceramic material. It was realized that it may be possible to produce a satisfactory restoration by forcing a molten or plastic glass-ceramic material into a mold having a cavity in the form of the desired dental restoration. The prior art further recognized that the glass-ceramic material could be introduced into the cavity when the glass-ceramic material was in the liquid or in the plastic state.

A constant goal of the prior art as described above was to effect the molding process in a quick and efficient manner, and in a manner that produces a dental restoration that has excellent definition and fit. In dental restorations, definition is extremely important. In order to have a satisfactory restoration, the finest details of the original tooth must be reproduced. For example, for a dental restoration to be successful, the margins must be sharp and well defined. It is in this area that the prior art molding processes are deficient, in that it was not possible to achieve the desired degree of definition.

Further, it is desirable to produce a dental restoration in a short period of time in order to efficiently utilize the overhead of the dental laboratory, and in order to minimize the labor content of the dental restoration.

Dental laboratories are not typically well funded operations. Therefore, in order to keep costs to a minimum, it is highly desirable that a suitable process for forming dental restorations utilize equipment which is relatively inexpensive. While the above described process fits this requirement, the below described DI-COR process does not.

As is discussed above, there are several prior art processes for the manufacture of dental restoration from glass-ceramic materials. A recent addition to the prior art is the DI-COR process as sold by Dentsply International, Inc., of York, Pa. In this process, a dental restoration is formed by centrifugal casting of a molten glass-ceramic material. This process is further described in U.S. Pat. No. 4,431,420, issued Feb. 14, 1984, and related patents. Centrifugal casting has been extensively used in the casting of metals principally by the lost wax process. Further, this process has been imminently successful for hundreds of years for use in conjunction with metals. This success results from the fact that molten metals have very low viscosity and high density in the molten state, hence, they function very well in centrifugal casting processes. That is, because molten metals have a high density and a very low viscosity in the molten state, centrifugal force is adequate for purposes of injecting the molten metal into a preformed mold cavity. In an attempt to produce dental restorations which have high definition, the above-mentioned DI-COR process uses centrifugal force to form the desired dental restorations from a molten glass-ceramic material. Molten glass-ceramic materials have a much higher viscosity, and a much lower density when compared to molten metals. For this reason, it is not possible to consistently drive a molten glass-ceramic material by centrifugal force alone into a mold in order to produce a satisfactory dental restoration. That is, a molten glass-ceramic material cannot be driven by centrifugal force into a mold cavity with sufficient force in order to always get the required definition, which is necessary to form a satisfactory dental restoration. It is well recognized by one skilled in the art, that in order to have a satisfactory dental restoration, excellent definition must be achieved in order to recreate the desired margins, which are needed for the proper fit of a dental restoration into the human mouth.

Further, the DI-COR process is deficient as to the coloration of the glass-ceramic material utilized. The resulting DI-COR dental restoration had an undesirable white color and must be glazed in order to produce satisfactory human coloration. As a result, the coloration is only on the surface of the dental restoration. If adjustment by grinding is needed in the final installation of the restoration into the human mouth, the glazing is removed, thereby exposing the whitish base which contrasts with the glaze. This contrast is very unsatisfactory from an esthetic point of view.

In contrast to this deficiency, the restoration of the subject process is adapted to utilize glass-ceramic materials, wherein the coloration of the resulting dental restoration throughout approximates human tooth coloration. Hence, if grinding is necessary in final fitting, contrast between the surface of the dental restoration and the underlying base is not observed.

Undesirable contrast can also result from normal wear, wherein as a result of the grinding action of one tooth against another, the glaze is worn away. Again, this is not a problem in this invention as the preferred glass-ceramic material has a uniform, natural coloration throughout. It should also be noted that the restoration of the subject invention may be glazed to achieve the exact shade desired.

In contrast to the above-discussed prior art processes, the process of the subject invention utilizes a positive, mechanically applied force for purposes of injecting the molten dental glass-ceramic material into the preformed mold cavity.

For a dental glass-ceramic material to be satisfactory for use in the formation of dental restorations, the material should incorporate many of or all of the following properties:

(1) It must be inert and non-toxic in an oral environment.
(2) It must have sufficient structural integrity to resist the forces of mastication, and, generally, must have a 3-point M.O.R. of at least 30,000 PSI.
(3) It should be capable of being formed into forms which are compatible with the human anatomy using simple equipment.
(4) It should have esthetic qualities (coloration similar to human teeth with a slightly translucent appearance), which are compatible with human teeth, and, hence, should be monolithic or glazable.
(5) The glass-ceramic material must not absorb moisture or stain, and it must be stress corrosion resistant.
(6) The glass-ceramic material should have wear characteristics which are similar to natural human teeth, and should be compatible with other dental materials.
(7) The glass-ceramic must have dimensional stability and resist thermal shock during processing, and, in particular, it must have dimensional stability during subsequent heat treating processes wherein recrystallization is effected.
(8) The glass-ceramic material should be compatible from a thermal expansion point of view with metals, stains, glazes, etc., as are conventionally used-to-form dental restorations.
(9) In order to create an esthetically pleasing dental restoration, it may be necessary to alter the final dental restoration to the exact shape and shade desired. In order to effect these alterations, the dental restoration must be heated to a temperature of about 950° C. for each operation. Therefore, a satisfactory glass-ceramic material must be capable of withstanding multiple heat cycles to about 950° C.
(10) A suitable glass-ceramic material must be capable of retaining its structural integrity during heat treating.
(11) A suitable glass-ceramic material should have:
 a. Coefficient thermal expansions (C.T.E.) of 9 to $14.5 \times 10^{-7}/°$ C.
 b. Translucency of 2.5 to 4.0 on a visible scale of 0 (clear) to 5 (opaque) and overall beauty;
 c. M.O.R. of at least 30 K.S.I. average;
 d. Ability to be heat treated to 925–950° C.;
 e. Structural integrity during heat treatment;
 f. Meltability and formability;
 g. Chemical durability in an oral environment.

The subject invention includes glass-ceramic materials which meet the above set forth criteria.

SUMMARY OF THE INVENTION

In accordance with the above description, it is obvious that in accordance with the prior art, it is difficult, if not impossible to form top quality dental restorations by molding glass-ceramic materials in an inexpensive and efficient manner.

The process, apparatus, compositions and dental restoration of the subject invention provide improvements over the prior art. By use of the process of the subject invention, glass-ceramic materials can be readily molded into dental restorations. Further, the apparatus of the subject invention is relatively inexpensive and is easy to utilize. The compositions of the subject invention are highly advantageous in that they produce esthetically pleasing dental restorations which are chemically inert in the human mouth, and have outstanding strength properties. Further, the compositions of this invention are advantageous in that when dental restorations formed from these compositions are heat treated, they maintain their structural integrity. Further, these dental restorations are capable of withstanding multiple heat cycles to about 950° C., possess thermal expansions which are compatible with the existing porcelains and therefore, these dental restorations can be readily altered using conventional porcelain materials.

Likewise, dental restorations in accordance with the present invention, have acceptable coloration after heat treating, and can be used at that stage without further cosmetic treatment in the mouth. In order to enhance the esthetic properties of the resulting dental restoration, the dental restoration can be readily altered using porcelain materials to achieve any desired effect.

Accordingly, it is an object of the present invention to provide an efficient process whereby dental restorations may be molded from glass-ceramic materials.

It is a further object of the present invention to provide glass-ceramic dental restorations which have outstanding strength and are esthetically pleasing.

It is also an object of this invention to provide glass-ceramic compositions which are suitable for the formation of dental restorations which have a high degree of microstructural control during the development of the crystals, thereby permitting great flexibility in forming these dental restorations.

It is still another object of this invention to provide a glass-ceramic material which will maintain its structural integrity during heat treating, and, in particular, will not slump or sag during heat treating outside of the investment.

Another object of the present invention is a glass-ceramic material which is suitable for the formation of dental restorations, and which is capable of maintaining its translucency during multiple firing cycles to approximately 950° C.

Still another object of this invention is a process for forming a ceramic dental restoration wherein the process comprises:

(1) Placing a glass-ceramic material in a heat-pressure deformable crucible;

(2) Heating the crucible and glass-ceramic material to a temperature at which said crucible becomes heat-pressure deformable, and the glass-ceramic material is moldable;

(3) Bringing the heatrf crucible into contact with a mold having a preformed cavity therein;

(4) Continuing to move the crucible into contact with the mold, thereby causing the crucible to deform against the mold and causing the moldable glass-ceramic material to be injected into said cavity, thereby forming a dental restoration;

(5) Cooling the mold and the ceramic dental restoration therein;

(6) Removing the formed ceramic restoration from the mold;

(7) Heat treating the dental restoration; and (8) Finishing the dental restoration.

Also, and object of this invention is to form a heat deformable crucible having a base and a side portion, wherein said crucible is formed by the heat sintering of a particulate mixture of glass and a metal oxide. A preferred composition comprises from about 27 to 31 percent glass, and from about 69 to about 73 percent of a metal oxide.

Another object of this invention is a dental restoration which is formed from a glass-ceramic material having the following composition (by weight percent):

| | |
|---|---|
| $Li_2O$ | 8–15 |
| $Al_2O_3$ | 1.5–5.0 |
| $SiO_2$ | 60–85 |
| $Na_2O$ | 0–2 |
| $K_2O$ | 0–2 |
| $P_2O_5$ | 1.5–5 |
| $ZrO_2$ | 0–3 |
| CaO | 0–1 |
| $BaO + SrO + La_2O_3$ | 0–12 |
| Coloring Oxides | 0–5 |

Still another object of this invention is a dental restoration which is formed from a glass-ceramic material having the following composition (by weight percent):

| | |
|---|---|
| $Li_2O$ | 14–15 |
| $Al_2O_3$ | 4.5–5.0 |
| $SiO_2$ | 67–71 |
| $Na_2O$ | 1–2 |
| $K_2O$ | 1.5–3.5 |
| $P_2O_5$ | 3–4 |
| $B_2O_3$ | 0–2 |

| -continued | |
|---|---|
| CaO | 0–1.25 |
| BaO | 1.25–3 |
| $Tb_4O_7$ | 0–1 |
| $CeO_2$ | 0–1 |

Lastly, an object of the present invention is to create a glass-ceramic material which has excellent chemical durability, and as such, will not deteriorate when exposed to the fluids in the human mouth.

These, and other objects, features, and advantages of the present invention, will become apparent from the detailed description herein.

The advantages of the present invention can be more clearly understood from the following description taken together with the drawings.

BRIEF DESCRIPTION OF THE DRAWINGS

FIG. 2 shows a sectioned lost wax mold for use in the invention;

FIG. 3 shows a sectioned structure illustrating the heating step of this invention;

FIG. 4 shows a sectioned structure illustrating the initial contact of the crucible with the mold;

FIG. 5 shows a sectioned structure illustrating the partial sealing of the crucible against the mold;

FIG. 6 shows a sectioned structure illustrating the complete sealing of the crucible against the mold, and the injection of the molten glass-ceramic into the mold cavity;

FIG. 8 shows a sectioned alternate mold;

FIG. 9 shows a sectioned alternate mold; and

FIG. 10 shows the mold of FIG. 9 being filled with a molten glass-ceramic material.

It should be noted that FIGS. 2 through 10 are schematic representations of apparatus which may be useful in this invention.

DESCRIPTION OF THE PREFERRED EMBODIMENT

Figure 1:
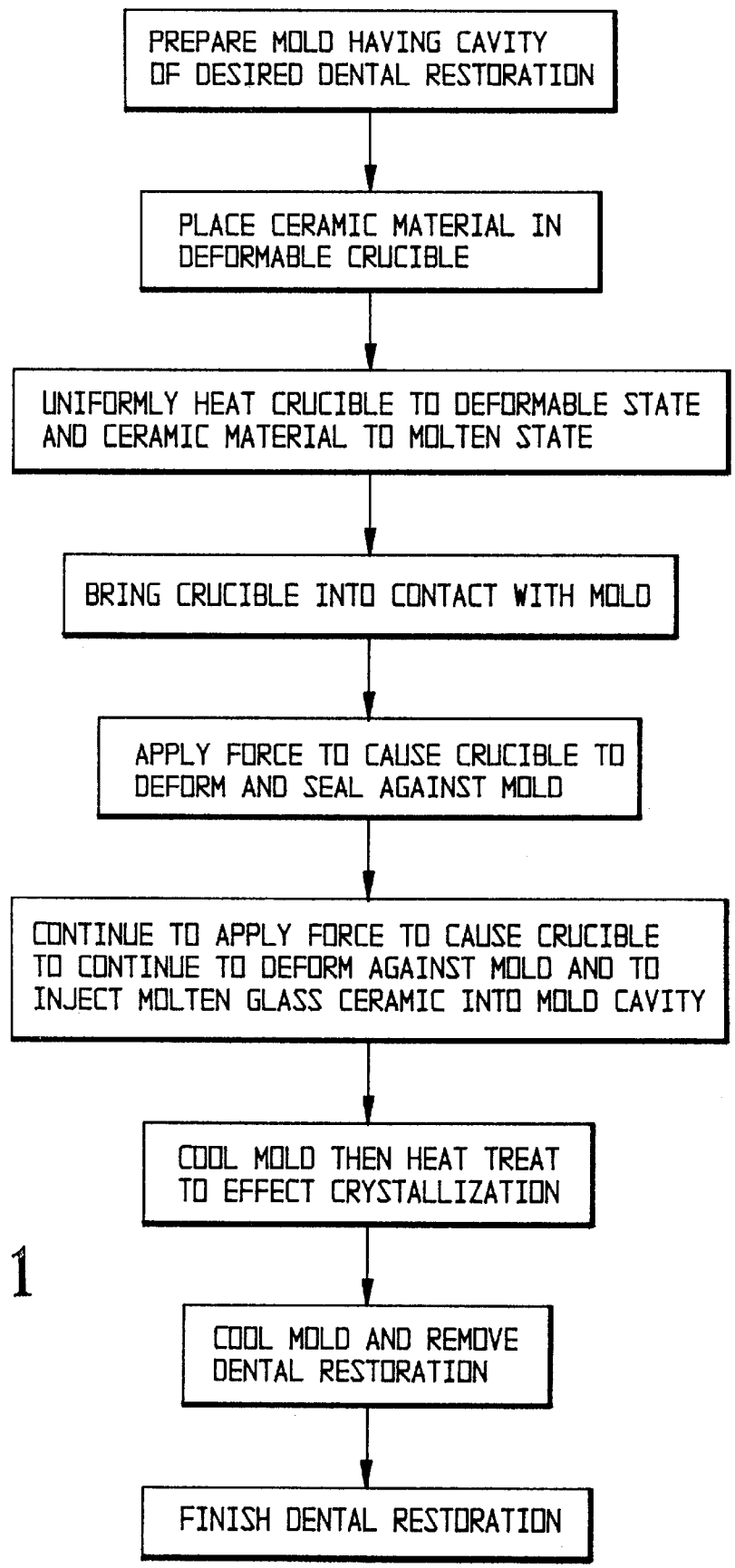
FIG. 1 is a flow chart showing the steps of the preferred embodiment of the process of this invention.

FIG. 1 generally described the overall process of the subject invention, wherein the dental restorations are formed by the molding of a glass-ceramic material. As can be seen in FIG. 1, the first step is the formation of a mold having a suitable mold cavity therein. To start the process whereby the mold cavity is formed, the tooth or teeth in the human mouth are prepared by the dentist by procedures which are commonly known in the prior art. By using impressions which are provided by the dentist, a positive wax form is then formed and positioned in a mold usually called a ring. A semi-liquid investment material is then poured around the positive wax form. Once the investment material sets up and cures, the resulting mold is placed in a furnace and heated, thereby causing the wax to melt and run out of a sprue hole which is integral with the mold. The finished mold is then complete. This constitutes the formation of a mold by the lost wax process.

In the second step of FIG. 1, a button of a glass-ceramic material is placed in deformable crucible 8, as is illustrated in FIG. 3. The button of a glass-ceramic material constitutes a small cylinder of the glass-ceramic material which usually weighs about six grams, and has a diameter of about two cm, and a thickness of about one cm. These buttons of glass-ceramic materials are a convenient shape, whereby these materials may be manufactured, sold and used. It is understood by one skilled in the art that a sufficient amount of the glass-ceramic material must be used in order to form the desired dental restoration.

In the third step of FIG. 1, crucible 8 and the button of the glass-ceramic material 7 is uniformly heated. The glass-ceramic material is heated to a temperature above its liquidus temperature, as will be described in greater detail herein below. Further, the heat-pressure, deformable crucible 8 will be described in greater detail herein below.

In the process of this invention, the preformed mold can incorporate multiple cavities in order that more than one dental restoration can be produced during one cycle of the subject process.

In steps four, five and six of FIG. 1, the heated crucible and glass-ceramic material are moved into contact with the mold by mechanical means in a manner which will be described in greater detail relative to the discussion of FIGS. 3 through 6 herein below.

In accordance with steps 7 and 8 of FIG. 1, the mold is cooled and the solidified glass-ceramic casting is removed from the investment by mechanical means. The dental restoration is then cut off the sprue and finished by heat treating, polishing, and/or glazing in order to achieve the desired esthetic effect.

The process of this invention may utilize both glass and glass-ceramic materials for purposes of forming the desired dental restoration.

For strength and esthetic reasons, it is preferred that a glass-ceramic material be utilized. When a glass-ceramic material is utilized, the button of glass-ceramic material 7 is initially placed in crucible 8 in a glass phase. As heat is applied to crucible 8, glass-ceramic material 7 becomes a ceramic via the formation of a crystalline phase. As the heating is continued, the glass matrix slowly dissolves the crystalline phase, thereby causing the glass-ceramic material 7 to re-enter the glass phase. The temperature at which the crystal phase completely dissolves in the glass matrix is defined as the liquidus temperature of the glass-ceramic material. In accordance with this invention, it is found desirable to heat the glass-ceramic material to a temperature above the liquidus temperature in order to eliminate any possibility of the existence of a crystalline phase in the molten material. Further, at this temperature, the glass-ceramic material has a viscosity of about log 3 to about log 4P, which is suitable to allow the molten glass-ceramic material to be readily injected into the mold cavity 5. The viscosity at this temperature is defined as the working range.

Throughout this application, the viscosity of the molten glass-ceramic materials and of the soften crucible will be defined as the log of the respective viscosity in poises. Further, the unit poise will be abbreviated as "P". For example, if the viscosity of a molten glass-ceramic material is $10^4$ poises, the viscosity will be indicated by log 4P.

While FIG. 1 illustrates the broad process of the subject invention, the individual steps as illustrated in FIG. 1 are defined in greater detail in the description of FIGS. 2 through 10.

In FIG. 2, it can be seen that mold 4 has been formed by the placement of an investment material 10 in ring 12. Prior to the placement of investment material 10 in ring 12, ring 12 is positioned around wax form 14, the upper extremity of which is shaped in the form of a desired dental restoration 16. Wax form 14 is only shown in an outline form, as FIG. 2 illustrates a finished mold 4 after wax form 14 has been burnt out.

The procedure whereby mold 4 is formed is generally known in the prior art, and has been used for centuries to form lost wax molds for use in metal casting procedures. As is stated above in the preparation of mold 4, wax form 14 is positioned in ring 12. An investment slurry 10 is then slowly poured into ring 12, usually with the aid of vibratory techniques to insure that investment 10 completely fills ring 12, and in particular, completely encases wax form 14. Again, these procedures are commonly known in the prior art.

FIGS. 3, 4, 5 and 6, show the general process of the subject invention in a schematic form.

Referring to FIG. 3, it can be seen that mold 4 having cavity 14 is positioned in the vicinity of crucible 8. Positioned in crucible 8 is glass-ceramic material 7, the details of which will be described herein. Crucible 8 is further positioned on a ceramic base 21 which is positioned on ram 22, whereby crucible 8 can be moved in relation to mold 4. An electric heating element 24 is further provided whereby heat can be applied to crucible 8. Details of the heating of glass-ceramic material 7 will be discussed herein below.

During the heating of crucible 8, glass-ceramic material 7 is converted from the solid state to the liquid state, and crucible 8 is converted from a solid, brittle state to a plastic state wherein it is heat-pressure deformable. Once the glass-ceramic material 7 reaches the desired working range, ram 22 is actuated as is illustrated in FIG. 4, thereby causing crucible 8 to move upwardly and to come into contact with the lower extremities of mold 4. The actuation of ram 22 is effected by a power source not shown.

As can been seen in FIG. 5, as the upward movement of ram 22 continues, crucible 8 continues to deform against mold 4 causing the upper extremities of crucible 8 to seal against mold 4 at interface 28. Further, it can be seen that molten glass-ceramic material 7 has started to flow into mold cavity 14.

Referring to FIG. 6, as the travel of ram 22 continues, the deformation of crucible 8 against mold 4 is completed, and cavity 14 is completely filled with glass-ceramic material 7 as a result of the applied pressure of ram 22.

Subsequent to the procedures as are illustrated in FIGS. 3 through 6, mold 4 is then cooled and the desired dental restoration is removed from the investment 10. Once the dental restoration is removed from investment 10, the dental restoration is cut apart from the sprue, and is heat treated and finished by polishing and glazing, in order to achieve the desired esthetic effect.

Further, after formation, dental restoration 26 is heat treated in such a manner that its strength and other properties are enhanced by the formation of crystals in a glass matrix. The details of heat treating are described below.

Figure 7:
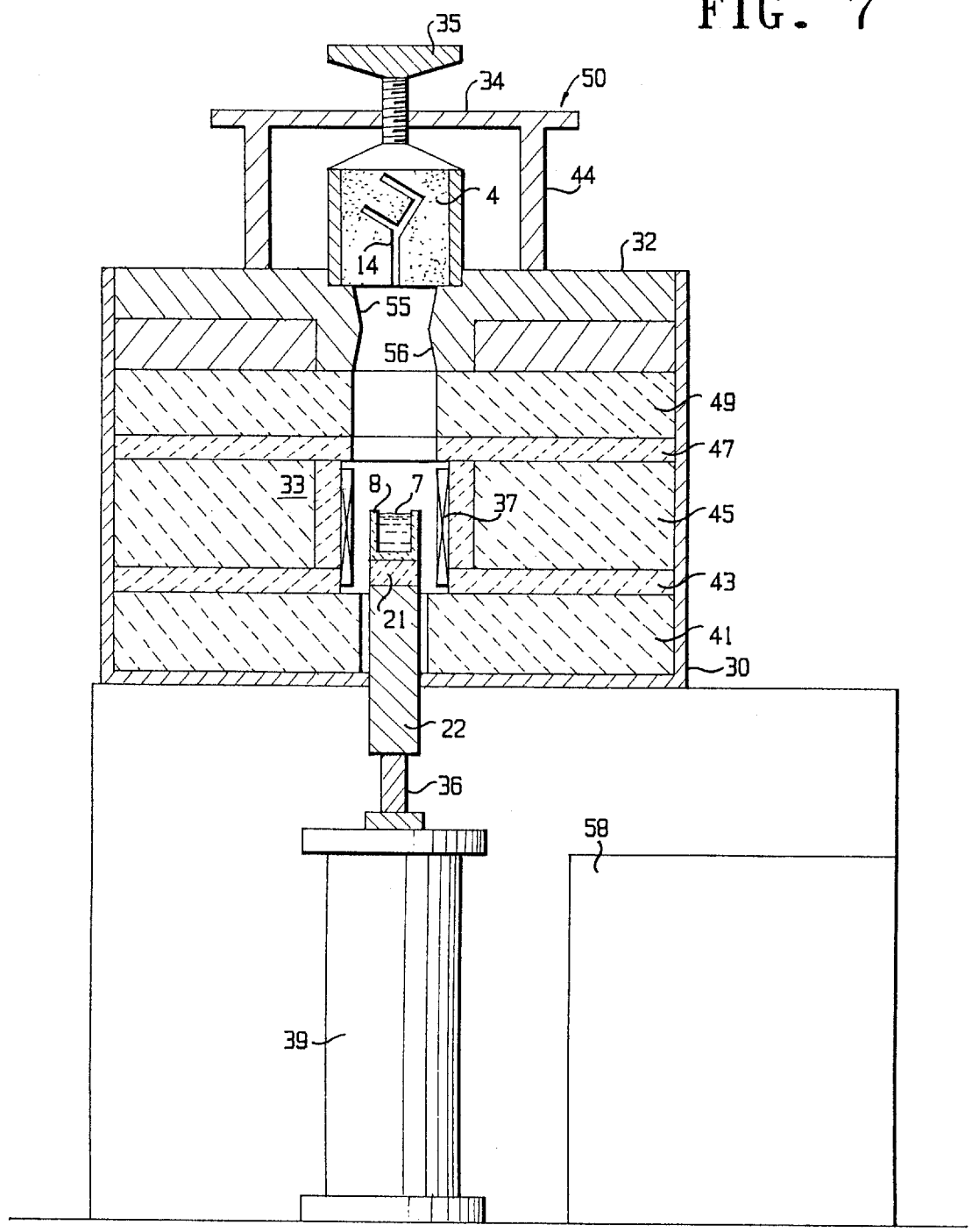
FIG. 7 is a sectioned side view showing the composite apparatus of this invention.

FIG. 7 illustrates apparatus 32 which may be utilized to effect the composite process which is illustrated in the flow chart of FIG. 1. This apparatus generally comprises support frame 30, heat source 33, mold retaining means 34, and a plunger 36. Support frame 30 generally comprises the outside frame of apparatus 32.

Mold retaining means 34 comprises a bar 50 into which is threaded mold clamp 35. As can be seen, bar 50 permits mold 4 to be locked to support bar 44. Support bar 44 further incorporates an aperture 56 which is slightly smaller than the diameter of mold 4 and slightly larger than the diameter of crucible 8. By the actuation of ram 36, crucible 8 is moved up into contact with mold 4 in a manner which is similar to that as is described above in conjunction with FIGS. 4, 5 and 6. The apparatus of FIG. 7 further incorporates a heat source 33, which in the illustrated embodiment comprises an electric resistance heating element 37. In the preferred embodiment, the heating element is molybdium disilicide. Heat source 33 is controlled by a power control source 58.

As is illustrated in FIGS. 3 and 7, an electric resistance heater may be utilized to effect the heating of crucible 8, and hence, glass-ceramic material 7. In addition to the electric resistance heating as illustrated, heating may be effected via induction heating, gas torch heating, or any other appropriate means.

The apparatus further may incorporate a rotating means (not shown), whereby ram 36 may be rotated during the heating process in order to effect a more uniform heating of crucible 8 and glass-ceramic material 7 contained therein. The rotating means may be an electric, pneumatic or hydraulic motor. Ram 36 is further provided with means for effecting its upward movement, which in the preferred embodiment, is a pneumatic cylinder 39.

Further, referring to FIG. 7, it can be seen that apparatus 32 incorporates a plurality of structural insulating members 41, 43, 45, 47 and 49, which support and contain heating element 37, and contain the heat created during the operation of the element 37. These structural insulating members are formed from ceramic fiber board.

Likewise, it can be seen that support bar 44 incorporates an aperture 56 which has a waist section 55. Waist section 55 is advantageous in that when crucible 8 deforms against mold 4, the deforming upper extremities of crucible 8 are prevented from downward movement at the constriction of waist 55, thereby causing the molten glass-ceramic material to be efficiently injected into the preformed cavity 14 in mold 4. That is, because when the upper extremities of crucible 8 are caused to solidify in the vicinity of waist 55, the downward movement of the molten glass-ceramic material is prevented, thereby causing the glass-ceramic material to be injected into mold cavity 14.

Figure 7A:
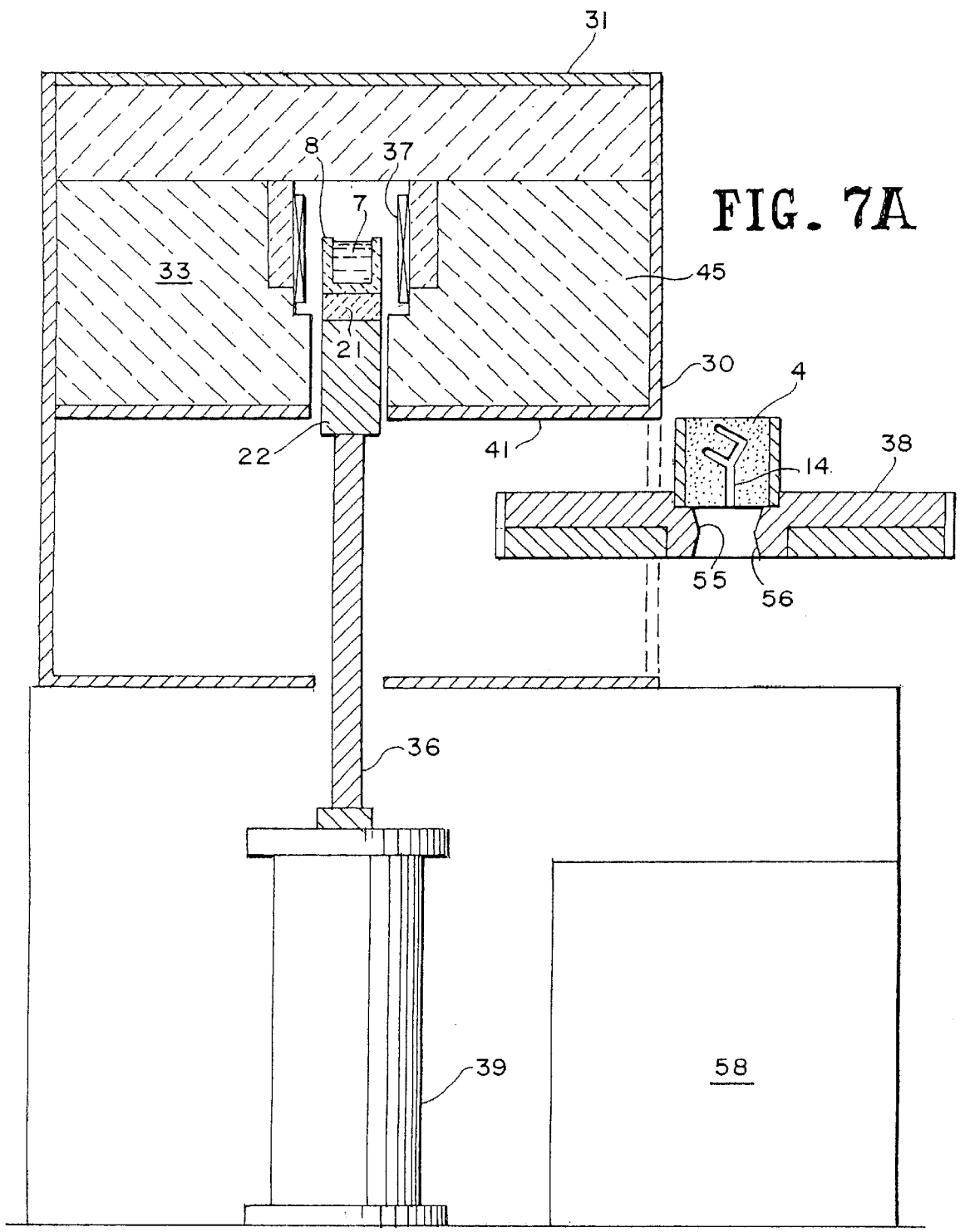

FIGS. 7a and 7b represent the preferred apparatus 31 for use in accordance with this invention. Most of the components of the preferred apparatus 31 are identical or similar to the components from apparatus 32; primarily, in that a movable arm 38 is provided for wherein a preheated mold 4 may be brought into position for the molding process and positioned against furnace base 41. Movable arm 38 may be connected to a central pivot point whereby it may be swung into position or it can be laterally moved into position.

Prior to moving arm 38 into position, as is shown in FIG. 7, a ram 22 is extended in order to place crucible 8 in heat source 33, whereby glass-ceramic material 7 may be melted. Once this melting is effected, ram 22 is withdrawn and movable arm 38 is swung into place to the position as is illustrated in FIG. 7b. In this position, the forming sequence, as is shown in FIGS. 2 through 6, can be completed.

Relative to apparatus 31 and 32, it is understood by one skilled in the art that crucible 8 may be placed in position on ceramic base 21 either manually or by automatic means.

The injecting of the glass-ceramic components of this invention can be effected using the apparatus as is illustrated in FIGS. 2 through 10, and is described herein above. In addition, a commercially available press as is sold under the trademark AUTOPRESS™ Plus, and as sold by Jeneric/Pentron of Wallingford, Conn. may be utilized. This system does not utilize a deformable crucible.

It is preferred that the glass-ceramic components of this invention be pressed under a vacuum of about 2 to about 8 bar with the preferred vacuum being 7 bar.

The above described FIGS. 1 through 7b, illustrate the formation of a dental restoration. In addition to being useful in the formation of essentially complete dental restorations, the composition and process of the subject invention may be used to form coping over which porcelain materials may be applied to alter and shade the dental restoration.

In the prior art, metal copings are extensively utilized. These copings are covered with layers of porcelain materials which are applied to the metal copings for purposes of forming a composite dental restoration which comprises a metal base and a porcelain exterior portion. Composite structures are advantageous in that a metal coping significantly enhances the strength of the resulting dental restoration. Metal copings are disadvantageous in that they are opaque and they have a color which contrasts with the color of a natural tooth, and further, they have toxicity problems in some instances. The use of the subject invention to form an all glass-ceramic dental restoration is advantageous in that the coping is essentially the same color as a natural tooth, and in particular, it is essentially the same color as the porcelain from which the exterior portion of the dental restoration is formed. Further, the all ceramic structure is advantageous in that problems resulting for certain patients who are allergic to certain metals are eliminated. In this procedure, metal free crowns and bridges of outstanding strength and esthetic properties are achieved. The outstanding esthetic properties result from the fact that these glass-ceramic copings can be utilized as a base over which a variety of different porcelains can be fired in order to achieve the most delicate coloration and esthetic properties.

As is stated above, the process of the invention may utilize both glass and glass-ceramic materials. Preferred glass-ceramic compositions for use in accordance with the invention are listed in Tables I to IVb. All components listed in Tables I to IVb are in weight percent.

The subject invention can utilize any suitable glass-ceramic material. As is shown in Tables I to IVb, preferred glass-ceramic materials for use in this invention are lithium disilicate glass-ceramic materials. In these materials, $Li_2O$ $2(SiO_2)$ constitutes the crystalline phase of the heat treated glass-ceramic material. Lithium disilicate glass-ceramic materials are particularly suited for use in the invention in that they are non-toxic, they resist thermal shock, have excellent strength, are corrosion resistant, and they produce dental restorations which approximate human coloration, are translucent, and esthetically pleasing. Further, lithium disilicate glass-ceramic materials are advantageous in that they maintain their structural integrity during heat treating, given that they do not slump or sag during proper heat treating.

Other lithium disilicate glass-ceramic materials which may be used in the process of this invention are disclosed in U.S. Pat. No. 5,219,799, issued Jun. 15, 1993.

Lithium disilicate glass-ceramic materials may utilize $P_2O_5$ as a nucleating agent. Other nucleating agents are $TiO_2$ and $ZrO_2$.

Glass-ceramic compositions which may be useful in this invention are as per Table I. The percentages of Table I and the other tables herein are in weight percent.

TABLE I

| | |
|---|---|
| $Li_2O$ | 8–15 |
| $Al_2O_3$ | 1.5–5.0 |
| $SiO_2$ | 60–85 |
| $Na_2O$ | 0–2 |
| $K_2O$ | 0–2 |
| $P_2O_5$ | 1.5–5 |
| $ZrO_2$ | 0–3 |
| CaO | 0–1 |
| $BaO + SrO + La_2O_3$ | 0–12 |
| Coloring Oxides | 0–5 |

More specific, glass-ceramic compositions which may be useful in the invention are as per Table II. In particular, the compositions of Table II are useful in conjunction with either high or low fusing porcelains which may be used to alter, shade or glaze the dental restorations of this invention.

TABLE II

| | |
|---|---|
| $Li_2O$ | 10–13.5 |
| $Al_2O_3$ | 2–3 |
| $SiO_2$ | 70–84 |
| $K_2O$ | 0–1 |
| $P_2O_5$ | 1.5–4 |
| $ZrO_2$ | 0–1 |
| $BaO + SrO + La_2O_3$ | .5–4 |
| CaO | 0–1 |
| Coloring Oxides | 0–5 |

In some instances, it is desirable to form a dental restoration which can be altered or glazed with a low fusing porcelain. For purposes of this application, a low fusing porcelain is defined as a porcelain which fuses at a temperature of about 700° C.

Specific glass-ceramic compositions which are useful in conjunction with low fusing porcelains are as per Table III.

TABLE III

| | |
|---|---|
| $Li_2O$ | 9–13 |
| $Al_2O_3$ | 1.5–4 |
| $SiO_2$ | 65–84 |
| $Na_2O$ | 0–1 |
| $K_2O$ | 0–1 |
| $P_2O_5$ | 1.5–4 |
| $ZrO_2$ | 0–1 |
| $BaO + SrO + La_2O_3$ | 0–12 |
| CaO | 0–1 |
| Coloring Oxides | 0–5 |

Specific glass-ceramic compositions which may be used in this invention are shown as per the attached Tables IV, IVa, and IVb.

TABLE IVa

| | |
|---|---|
| $Li_2O$ | 14–15 |
| $Al_2O_3$ | 4.5–5.0 |
| $SiO_2$ | 67–71 |
| $Na_2O$ | 1–2 |
| $K_2O$ | 1.5–3.5 |
| $P_2O_5$ | 3–4 |
| $B_2O_3$ | 0–2 |
| BaO | 1.25–3.0 |
| $Tb_4O_7$ | 0–1 |
| $CeO_2$ | 0–1 |
| CaO | 0–1.25 |

TABLE IVb

| | 21 | 22 | 23 | 24 | TOLERANCE |
|---|---|---|---|---|---|
| $SiO_2$ | 70.6 | 68.7 | 68.3 | 68.8 | ±1 |
| $Al_2O_3$ | 4.8 | 4.8 | 4.8 | 4.8 | ±.3 |
| Li2O | 14.7 | 14.4 | 14.5 | 14.4 | ±1 |
| $P_2O_5$ | 3.6 | 3.3 | 3.3 | 3.3 | ±.25 |
| CaO | 0.5 | 1.0 | 1.0 | 1.0 | ±2 |
| $K_2O$ | 2.0 | 2.0 | 2.0 | 2.0 | ±.25 |
| $Na_2O$ | 1.4 | 1.5 | 1.5 | 1.4 | ±.25 |
| BaO | 1.4 | 2.8 | 2.8 | 2.8 | ±.3 |
| $B_2O_3$ | 0.9 | — | 1.3 | 1.2 | ±.3 |
| $Tb_4O_7$ | — | 0.7 | — | — | ±.05 |
| $CeO_2$ | — | 0.7 | — | — | ±.05 |

In the formation of a dental restoration by a molding process it is desirable to have a glass ceramic composition which will readily flow into a mold in order to create the finest details of the dental restoration. This fact is true regardless of the molding process which is utilized.

The compositions of this invention may be pressed into a dental restoration in either a glass or a glass ceramic phase. When the pressing is effected in the glass phase the resulting dental restoration is subsequently heat treated to convert the structure to a glass ceramic phase.

In some cases it is desirable to press the compositions of this invention as a glass ceramic. The ability to press or inject the composition of this invention as a glass ceramic into the complex shapes of dental restoration is facilitated by the presence of residual glass in the range of from about 15 to 60 percent by volume. This residual glass functions as a matrix for the lithium disilicate crystalline phase.

For purposes of forming dental restoration, in accordance with this invention, when the composition is in the glass ceramic phase the glass ceramic pellets or buttons are preheated to a temperature of from about 850° C. to 950° C., with a most preferred preheat temperature being less than 930° C.

The compositions of Tables IVa and IVb have been modified in accordance with the prior art in order to increase their flowability, as a glass ceramic, in comparison to the compositions of Tables III and IV, comparing the composition of tables III and IV to the compositions of Tables IVa and IVb it can be seen that in the latter mentioned tables the composition of these tables incorporate $B_2O_3$. In the compositions of Tables IVa and IVb the $B_2O_3$ functions as a glass modifier for the glass phase of the glass ceramic. In this regard the $B_2O_3$ softens the glass matrix and increases its flowability thereby aiding the flowability of the crystal phase in the molding process. This known property of $B_2O_3$ produces a superior glass ceramic for use in accordance with this invention.

Zinc oxide is still another oxide which is safe in a dental environment which can be used to soften the glass matrix in order to facilitate the flow of the crystal phase during the molding operation.

The compositions as listed above incorporate $Li_2O$ which again softens the glass matrix and aides in crystal flow. The compositions of this invention incorporate substantial quantities of $Li_2O$ which likewise can function as a softener for the glass matrix. In the composition of this invention it is thought that the $Li_2O$ does not soften the glass matrix as all of the $Li_2O$ is used in the formation of the crystal phase. The fact that $B_2O_3$ lowers the viscosity (softens) silicate glass systems and produces glasses which have low thermal expansions and high chemical resistance is discussed in

*SILICATE GLASS TECHNOLOGY METHODS* by Clarence L. Babcock, John Wiley & sons 1977 at page 23.

Relative to the above discussion of the fact that $Li_2O$, $Na_2O$, $K_2O$ and $B_2O_3$ function to decrease viscosity and thereby soften glasses see also MODERN GLASS PRACTICE by Samuel R. Scholes, Industrial Publications, Inc. 1952 at page. 17.

Further as these references disclose it is known in the prior art that the oxides of sodium and potassium act as glass modifiers and thereby aid in crystal flow during the molding of a glass ceramic. In this regard comparing the compositions of Tables III and IV with the compositions of Tables IVa and IVb it can be seen that in the compositions of Tables IVa and IVb the percentages of $Na_2O$ and $K_2O$ have been increased, compared to the compositions of Tables III and IV. Again in accordance with known procedures this increase in the concentration of $Na_2O$ and $K_2O$ softens the glass matrix and thereby aids in the flowability of the crystal phase.

In summary the compositions of Tables IVa and IVb are altered with glass modifiers in such a manner as to aid in the flowability of the crystal phase. It is understood by one skilled in the art that glass modifies other than these discussed above can be utilized.

As to a general range of compositions which are preferred for use in conjunction with this invention, the glass-ceramic compositions as defined in Tables IVa and IVb are preferred.

The most preferred glass-ceramic composition for use in accordance with this invention is the glass-ceramic composition as is defined by compositions 21–24 in Table IVb.

The glass-ceramic composition as defined by Tables I to IVb above are particularly advantageous over the prior art in that:

(1) They are stronger than the prior art glass-ceramic compositions;
(2) Those compositions which incorporate $Tb_4O_7$ and cerium oxides are fluorescent in ultra violet light;
(3) The expansion rates of many of these glass-ceramic compositions are compatible with the expansion rate of existing altering porcelain materials; and
(4) They retain their structural integrity at higher temperatures than those of the prior art, thereby permitting alterations at higher temperatures.

Buttons of glass-ceramic materials in accordance with this invention are formed by first preparing a master batch of the components of the particular glass-ceramic desired. This batch is used to form a homogenous glass-ceramic which, upon cooling, is ground into a powder. Portions of this powder are then fused or sintered to form buttons of the desired size and weight. Relative to these sintered buttons, the applicant has found that dental restorations which are formed from solid, non-sintered buttons are stronger than those formed from sintered buttons. These buttons can assume the shape of blocks which may be milled into dental restorations by conventional, three-dimensional milling procedures in accordance with known prior art procedures.

As is listed in Tables I to IVb, coloring oxides may be added to the glass-ceramic material in order to achieve the desired coloration of the glass-ceramic dental restorations.

Suitable coloring oxides for use in glass-ceramic compositions which can be used in this invention, some of which are illustrated in Tables I to IVb, are $SnO_2$, MnO, CeO, $FeO_2$, $Ni_2O$, $V_2O$, $Cr_2O_3$, $TiO_2$, etc. These coloring oxides may be used singularly or in combination.

In addition to coloring oxides, the glass-ceramic compositions of Tables I to IVb may incorporate fluorescing agents and opacifiers. After formation of a glass-ceramic restoration in accordance with the process of this invention, the resulting dental restoration is heat treated in order to effect the formation of crystals in the dental restoration. This crystal formation is generally referred to as heat treating and enhances the physical and esthetic properties of the dental restoration. A suitable heat treating sequence for use with the glass-ceramic compositions of Tables I to IVb is as per Table V below.

For the glass compositions which may be used in this invention, the best nucleating temperatures are about 25° to 50° C. above the upper annealing point of the glass-ceramic. It has also been determined that a slow increase in temperature from just above the upper annealing point to some 50° C. or higher, produces the best results in achieving maximum nucleation. It is also well known that the temperature then must be raised to a higher temperature to affect crystallization. This temperature depends upon the composition of the particular glass-ceramic material being used.

If the heating sequence in the heat treating stage is improper or is incorrectly controlled, the dental restoration may slump or deform. It is understood by one skilled in the art that an optimum heat treating procedure should be developed for each particular glass-ceramic material in order to allow the dental restoration to maintain its structural integrity during the heat treating process.

In the preferred embodiment, the heat treating cycle is such that in the crystalline phase, the glass-ceramic material incorporates a large number of fine crystals which are evenly dispersed throughout the glass matrix. It has been found that when the crystalline phase is very fine and evenly dispersed, a dental restoration of maximum strength results. Further, a fine crystalline structure tends to produce translucent dental restorations.

From the above discussion, it is obvious that dental restorations produced in accordance with this invention can be heat treated after the dental restoration is removed from the investment material and the sprue is cut away.

In accordance with an alternate preferred embodiment of this invention, the heat treating of the dental restoration may be effected while the dental restoration is still in the invested state. That is, heat treating can be effected while the dental restoration is still encased in the investment material.

In accordance with still another embodiment, the dental restoration can be removed from the investment material in which it was formed and finished or partially finished prior to heat treating. For heat treating, the material is then reinvested in an investment material which enhances the heat treatment process. After reinvestment, the heat treating is carried out in accordance with the procedure described above.

When the dental restoration is heat treated in the invested state, the shrinkage of the dental restoration is minimized, if not eliminated.

In heat treating, and, in particular, in the formation of a crystalline phase, shrinkage of the dental restoration occurs. This shrinkage can amount to 3 percent. Naturally, this shrinkage is undesirable as it adversely affects the fit of the dental restoration back into the patient's mouth.

As a way of overcoming the shrinkage problem, it is within the scope of this invention to invest the wax form in an investment material which expands when it hardens to produce an oversized mold cavity. This oversized mold cavity naturally produces an oversized dental restoration. This oversized dental restoration is then shrunk back to the correct size during the heat treating process.

For example, since the glass-ceramic material shrinks about 3 percent during the heat treating process, the original wax form may be invested in an investment which expands by 3 percent when it hardens. Using this procedure, a dental restoration which is 3 percent oversized results. This oversized dental restoration is then heat treated, whereupon it shrinks about 3 percent to produce a finished dental restoration of the correct size.

In order to achieve proper fit, if the restoration is to be heat treated after removal from the investment, an investment material which expands on hardening and heating by about 3 percent must be used. Investment materials which are useful with metals are not particularly suited for use in the invention as they only expand about 1.75 percent. Investments which expand about 3 percent upon hardening and heating, and hence permit this type of process, are manufactured by Whipmix Corporation of Louisville, Ky., and sold under the designation GIJM 2-23-94; 1.

The preferred heat treating process for use with the glass-ceramic compositions of Tables I to IVb is as per Table V.

TABLE V

| Heat Dental Restoration to | 500° C. |
|---|---|
| Ramp or Soak at | 500° to 600° C. for 2–6 hrs. |
| Ramp at | 600°–925° C. for 2–3 hrs. |
| Soak at | 925° C. for 1–2 hrs. |
| Cool to | Room Temperature |

After heat treating, the resulting dental restoration may be further finished. This finishing may include a step wherein the dental restoration is altered with one or more porcelains in order to achieve the precise shape, shade and shading desired. For those glass-ceramic materials of Table I to IVb, it is desired that the C.T.E. of the altering porcelain material be slightly more or less than the C.T.E. of the glass-ceramic material. This process wherein the C.T.E. is measured is defined in the description of the examples herein below.

Deformable crucible 8 is a critical part of the subject invention. Crucible 8 in its preferred embodiment has a circular base and, hence, is generally cylindrical. However, it is understood by one skilled in the art, that the crucible of this invention can have configurations other than circular.

The crucible is formed by heat sintering a particulate mixture of components, such as, fused silica, aluminum oxide, zirconium oxide, magnesium oxide with a glass such as borosilicate glass, soda lime glass, bottle glass, window glass, etc., clay or other materials that those skilled in the art of crucible making might use to form a crucible suitable for use with a glass-ceramic material. In the broad concept of this invention, one forms the crucible of a mixture of materials, such that at the temperature where the glass-ceramic material is in the working range of about log 3 to log 4P, the crucible has a viscosity of about log 5 to log 7P.

Crucibles for use in this invention are formed by slip casting. The formation of crucible by slip casting is well known to those skilled in the art, and is described in greater detail in the examples below.

In the description as set forth above, the compositions which are used to form crucibles which are useful in this invention, may utilize a wide range of materials. While many glasses can be used to form crucibles which are useful in the subject invention, because of their toxicity, glasses which contain heavy metals, such as lead, cadmium, etc., should not be used.

An alternate method for the formation of crucibles for use in this invention, is by powder pressing and then sintered.

In this invention, the composition from which the crucible is formed contains materials such that it will be heat-pressure deformable at the desired temperature, i.e., about log 3 to log 4P, working temperature of the glass-ceramic. The heat-pressure deformation properties of the crucibles used in this invention is to be contrasted with the crucibles of the prior art which are designed to be rigid at the working temperature of the glass-ceramic material which is contained therein.

In the alternate structure, as is shown in FIGS. 8, 9, and 10, the sealing of the deformed crucible against the mold is enhanced. In the structure as shown, mold 64 incorporates a circular depression 66 having vertical walls 68 and 70, to which crucible 8 may seal. Vertical walls 72 and 74 of mold 65 may further incorporate a plurality of annular grooves 76. As is further shown in FIG. 10, the sealing of crucible 8 against mold 65 is enhanced by the flowing of the upper extremities of crucible 8 into annular grooves 76 during the deformation process.

EXAMPLES

The present invention is illustrated by the following examples. However, these examples are not to be construed as limiting the invention.

Dental restorations were prepared in accordance with the below listed examples. In these examples, wax models of a tooth were prepared. A sprue was then attached to the wax model. The wax model with the sprue attached was then placed in an investment ring. An investment material was then prepared by mixing 90 grams of Kerr Thermovest with 17 ml of a mixture of 2 parts of Thermovest liquid with 1 part water. The resulting mixture was then mixed to a uniform consistency. The mixed investment was then vibrated into the investment ring and around the wax model. The mold was allowed to dry and harden overnight. The investment ring was then placed in a burn out furnace at room temperature, and the temperature raised to 600° C. whereupon the wax model was burned out of the investment material.

The crucibles as used in these examples were prepared by slip casting. In this process, a female plaster of Paris mold was prepared by mixing 1247.4 grams of plaster of Paris with 946 ml of water to a uniform consistency. The resulting mold was allowed to harden for 36 hours. A slurry of a particulate crucible formulation mixture, as is identified in the examples below, was then placed in the preformed plaster of Paris mold. The green crucible was removed from the mold and fired in a furnace for 15 minutes at 1100° C. to sinter the crucible to a hardened, more durable form.

The slurry used to form the crucible was formed by mixing 1 pound of particulate material with 160 ml water.

Because of the hygroscopic nature of the plaster of Paris mold, the particulate crucible formulation slurry coagulates in the plaster of Paris mold. When the desired crucible wall thickness was achieved, the remainder of the slurry was poured out of the mold resulting in a green crucible structure which was allowed to dry.

In the listed examples and in this application, the coefficient of thermal expansion (C.T.E.) was measured from room temperature to 250° C., and is reported in units of $\times 10^{-7}/°$ C.

The translucency of the resulting dental restoration was measured by visual inspection given a value of 0 to 5, wherein value of 0 was deemed to be perfectly clear and 5 was deemed to be opaque.

In the below listed examples, for purposes of injecting the molten glass and glass-ceramic material into the mold, a pressure of 30 P.S.I. was utilized, with the exception of examples 26 and 27, wherein a pressure of about 50 P.S.I. was utilized.

The referenced heat treating sequence for all examples, except examples 26 and 27, is in accordance with Table V above.

In the below examples, the glass-ceramic test rods for measuring modules or rupture (M.O.R.) and thermal expansion (C.T.E.) were formed along with color tab test samples. These test rods and color tab samples were subjected to the heat treatment process of Table V, whereby the glasses were crystallized unsuitable to glass-ceramics. The test rod samples were 0.120"×1.25". The examples also record the visual appearance of each glass-ceramic and values of various properties exhibited by the glass-ceramic, such as, linear coefficient of thermal expansion (C.T.E.), reported in terms of $\times 10^{-7}/°$ C. modules of rupture (M.O.R.), cited in terms of K.S.I. (thousands of pounds per square inch), as determined in accordance with measurement techniques conventional in the art. K.S.I. may be converted to its metric equivalent MPA by dividing K.S.I. by 0.145.

The components used in these examples are as follows:
a. Thermovest and Therovest liquid as sold by Kerr Manufacturing Co., Romulus, Mich.
b. 3I fused silica as sold by Harbison Walker Refractories Division of Indresco, Inc., Pittsburgh, Pa.
c. SP921 TF (borosilicate glass) as sold by Specialty Glass, Inc., of Oldsmar, Fla. and has the following compositions in weight percent:

TABLE VI

| | |
|---|---|
| $SiO_2$ | 78 |
| $B_2O_3$ | 15 |
| $Al_2O_3$ | 2.5 |
| $Na_2O$ | 4.5 |

Example 1

An attempt was made to form a glass-ceramic dental restoration in accordance with the following procedure. A mold was prepared in accordance with the procedure described above.

By use of slip casting techniques, a crucible was prepared in accordance with the procedure described above by mixing 90.9 grams of SP921 TF glass in 363.2 grams of 3I fused silica with 160 ml of water. After slip casting and drying, the crucible was sintered at a temperature of 1100° C. A glass button weighing 6 grams was then placed in the crucible and preheated to a temperature of 650° C.

The composition of the glass-ceramic material used is in accordance with composition #1 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6. The crucible cracked, and, hence, no dental restoration was formed.

Example 2

A glass-ceramic dental restoration was prepared in accordance with the following procedure. A mold was prepared in accordance with the procedure described above.

By use of slip casting technique, a crucible was prepared in accordance with the procedure described above by mixing 136.2 grams of SP921 TF glass and 317.8 grams of 3I fused silica with 160 ml of water. After slip casting and drying, the crucible was sintered at a temperature of 1100° C. A glass button weighing 6 grams was then placed in the crucible and preheated to a temperature of 650° C.

The composition of the glass-ceramic material used is in accordance with composition #1 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting dental restoration had excellent definition and a M.O.R. of 41 K.S.I., a C.T.E. of 148, a translucency of 3.6, and a softening temperature of 975° C.

During the forming process, the crucible retained its structural integrity, and formed an effective seal with the mold.

Further, during the heat treating process, the finished dental restoration retained its structural integrity and did not slump or deform during heat treating.

Additional tests were conducted, wherein it was determined that the crucible of this example deformed and sealed well at 1375° C. and 1425° C.

Example 3

A mold was prepared in accordance with the procedure described above.

By use of slip casting technique, a crucible was prepared in accordance with the procedure described above by mixing 181.6 grams of SP921 TF glass and 272.4 grams of 3I fused silica with 160 ml of water. After slip casting and drying, the crucible was sintered at a temperature of 1100° C. A glass button weighing 6 grams was then placed in the crucible and preheated to a temperature of 650° C.

The preheated crucible without glass-ceramic material was then placed in an apparatus which is similar to that shown in FIG. 7, and heated to a temperature of 1400° C. for a period of 10 minutes.

During the heating process, the crucible lost its structural integrity, and was not capable of effecting a seal with a mold. Therefore, no molding process was carried out.

Example 4

A mold was prepared in accordance with the procedure described above.

By use of slip casting technique, a crucible was prepared in accordance with the procedure described above by mixing 227 grams of SP921 TF glass and 227 grams of 3I fused silica with 160 ml of water. After slip casting and drying, the crucible was sintered at a temperature of 1100° C. A glass button weighing 6 grams was then placed in the crucible and preheated to a temperature of 650° C.

The preheated crucible and glass-ceramic material were then placed in an apparatus which is similar to that shown in FIG. 7, and heated to a temperature of 1400° C. for a period of 10 minutes.

During the heating process, the crucible melted, and, hence, was not capable of forming an effective seal with the mold. Therefore, no molding process was carried out.

Example 5

A glass-ceramic dental restoration was prepared in accordance with the following procedure. A mold was prepared in accordance with the procedure described above.

By use of slip casting technique, a crucible was prepared in accordance with the procedure described above by mixing 118 grams of SP921 TF glass and 336 grams of 3I fused silica with 160 ml of water. After slip casting and drying, the crucible was sintered at a temperature of 1100° C. A glass button weighing 6 grams was then placed in the crucible and preheated to a temperature of 650° C.

The composition of the glass-ceramic material used is in accordance with composition #1 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting dental restoration had excellent definition and physical properties, as are reported in Example 2.

During the forming process, the crucible retained its structural integrity, and formed an effective seal with the mold. Further, during the heating process, the finished dental restoration retained its structural integrity, and did not slump or deform. Further tests were conducted on crucibles having the composition as set forth above, wherein it was determined that the crucible cracked, and, hence, was not functional at 1375° C. An additional test demonstrated that the crucible of this example deformed and sealed at 1425° C.

Example 6

A glass-ceramic dental restoration was prepared in accordance with the following procedure. A mold was prepared in accordance with the procedure described above.

By use of slip casting technique, a crucible was prepared in accordance with the procedure described above by mixing 127.1 grams of SP921 TF glass and 336.9 grams of 3I fused silica with 160 ml of water. After slip casting and drying, the crucible was sintered at a temperature of 1100° C. A glass button weighing 6 grams was then placed in the crucible and preheated to a temperature of 650° C.

The composition of the glass-ceramic material used is in accordance with composition #1 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting dental restoration had excellent definition and physical properties, as are reported in Example 2.

During the forming process, the crucible retained its structural integrity, and formed an effective seal with the mold. Further, during the heating process, the finished dental restoration retained its structural integrity, and did not slump or deform. Further tests were conducted on crucibles having the composition as set forth above, wherein it was determined that the crucible would deform and seal at both 1375° C. and 1425° C.

Example 7

A glass-ceramic dental restoration was prepared in accordance with the following procedure. A mold was prepared in accordance with the procedure described above.

By use of slip casting technique, a crucible was prepared in accordance with the procedure described above by mixing 145.3 grams of SP921 TF glass and 308.7 grams of 3I fused silica with 160 ml of water. After slip casting and drying, the crucible was sintered at a temperature of 1100° C. A glass button weighing 6 grams was then placed in the crucible and preheated to a temperature of 650° C.

The composition of the glass-ceramic material used is in accordance with composition #1 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting dental restoration had excellent definition and physical properties, as are reported in Example 2.

During the forming process, the crucible retained its structural integrity, and formed an effective seal with the mold. Further, during the heating process, the finished dental restoration retained its structural integrity, and did not slump or deform. Further tests were conducted on the crucible of this example, wherein it was determined that the crucible functioned at 1375° C. However, at 1425° C., the crucible slumped, and, hence, could not be used in the process of this invention.

Example 8

A glass-ceramic dental restoration was prepared in accordance with the following procedure. A mold was prepared in accordance with the procedure described above.

By use of slip casting technique, a crucible was prepared in accordance with the procedure and description shown above in connection with example 2. A glass button weighing 6 grams was then placed in the crucible, and preheated to a temperature of 650° C.

The composition of the glass-ceramic material used is in accordance with composition #2 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition and a M.O.R. of 46.7 K.S.I., a C.T.E. of 138, a translucency of 2.75, and a softening temperature of 975° C.

During the forming process, the crucible retained its structural integrity, and formed an effective seal with the mold. Further, during the heat treating process, the finished dental restoration retained its structural integrity, and did not slump or deform during heat treating.

Example 9

A glass-ceramic dental restoration was prepared in accordance with the following procedure. A mold was prepared in accordance with the procedure described above.

By use of slip casting technique, a crucible was prepared in accordance with the procedure and description shown above in connection with example 2. A glass button weighing 6 grams was then placed in the crucible, and preheated to a temperature of 650° C.

The composition of the glass-ceramic material used is in accordance with composition #3 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition and a M.O.R. of 43 K.S.I., a C.T.E. of 141, a translucency of 3.0, and a softening temperature of 975° C.

During the forming process, the crucible retained its structural integrity, and formed an effective seal with the mold. Further, during the heat treating process, the finished dental restoration retained its structural integrity, and did not slump or deform during heat treating.

Example 10

A glass-ceramic dental restoration was prepared in accordance with the following procedure. A mold was prepared in accordance with the procedure described above.

By use of slip casting technique, a crucible was prepared in accordance with the procedure and description shown above in connection with example 2. A glass button weighing 6 grams was then placed in the crucible, and preheated to a temperature of 650° C.

The composition of the glass-ceramic material used is in accordance with composition #4 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition and a M.O.R. of 48 K.S.I., a C.T.E. of 133, a translucency of 2.5, and a softening temperature of 975° C.

During the forming process, the crucible retained its structural integrity, and formed an effective seal with the mold. Further, during the heat treating process, the finished dental restoration retained its structural integrity, and did not slump or deform during heat treating.

Example 11

A glass-ceramic dental restoration was prepared in accordance with the following procedure. A mold was prepared in accordance with the procedure described above.

By use of slip casting technique, a crucible was prepared in accordance with the procedure and description shown above in connection with example 2. A glass button weighing 6 grams was then placed in the crucible, and preheated to a temperature of 650° C.

The composition of the glass-ceramic material used is in accordance with composition #5 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then heat treated.

The resulting test samples and dental restoration had excellent definition and a M.O.R. of 42 K.S.I., a C.T.E. of 140, a translucency of 2.75, and a softening temperature of 975° C.

During the forming process, the crucible retained its structural integrity, and formed an effective seal with the mold. Further, during the heat treating process, the finished dental restoration retained its structural integrity, and did not slump or deform during heat treating.

Example 12

A glass-ceramic dental restoration was prepared in accordance with the following procedure. A mold was prepared in accordance with the procedure described above.

By use of slip casting technique, a crucible was prepared in accordance with the procedure and description shown above in connection with example 6. A glass button weighing 6 grams was then placed in the crucible, and preheated to a temperature of 650° C.

The composition of the glass-ceramic material used is in accordance with composition #6 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then heat treated.

The resulting test samples and dental restoration had excellent definition and a M.O.R. of 41.5 K.S.I., a C.T.E. of 162, a translucency of 4.0, and a softening temperature of 950° C.

During the forming process, the crucible retained its structural integrity, and formed an effective seal with the mold. Further, during the heat treating process, the finished dental restoration retained its structural integrity, and did not slump or deform during heat treating.

Example 13

A glass-ceramic dental restoration was prepared in accordance with the following procedure. A mold was prepared in accordance with the procedure described above.

By use of slip casting technique, a crucible was prepared in accordance with the procedure and description shown above in connection with example 6. A glass button weighing 6 grams was then placed in the crucible, and preheated to a temperature of 650° C.

The composition of the glass-ceramic material used is in accordance with composition #7 of Table IV.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition and a M.O.R. of 53.5 K.S.I., a C.T.E. of 136, a translucency of 4.0, and a softening temperature of 975° C.

During the forming process, the crucible retained its structural integrity, and formed an effective seal with the mold. Further, during the heat treating process, the finished dental restoration retained its structural integrity, and did not slump or deform during heat treating.

Example 14

A glass-ceramic dental restoration was prepared in accordance with the following procedure. A mold was prepared in accordance with the procedure described above.

By use of slip casting technique, a crucible was prepared in accordance with the procedure and description shown above in connection with example 2. A glass button weighing 6 grams was then placed in the crucible, and preheated to a temperature of 650° C.

The glass-ceramic material used was DI-COR, sold by the Dentsply Corporation, as is described above. DI-COR is thought to be fluoro-mica glass-ceramic.

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

The dental restoration was then heat treated in the investment.

While the glass-ceramic properly filled the mold, the resulting dental restoration cracked as a result of shrinkage during the heat treating process. This cracking is thought to be a result from the fact that the forming investment was not suitable for use in the heat treating sequence.

Example 15

A glass-ceramic dental restoration was prepared in accordance with the following procedure. A mold was prepared in accordance with the procedure described above.

By use of slip casting techniques, a crucible was prepared in accordance with the procedure and composition described above in connection with example 2. A glass button weighing 6 grams was then placed in the crucible, and preheated to a temperature of 650° C.

The composition of the glass used in weight percent was:

TABLE VII

| | |
|---|---|
| $SiO_2$ | 50.2 |
| $B_2O_3$ | 8.6 |
| $AlF_3$ | .7 |
| $Al_2O_3$ | 16.0 |
| BaO | 4.75 |
| ZnO | 19.75 |

The preheated crucible and glass-ceramic material were then placed in an apparatus which is similar to that shown in FIG. 7, and heated to a temperature of 1400° C. for a period of 10 minutes. The ram was then actuated, and the crucible was brought into contact with the mold in accordance with the general procedure as is illustrated in FIGS. 3 through 6.

A satisfactory dental restoration resulted, which was then removed from the investment material, and cut apart from the sprue.

The resulting test samples and dental restoration had excellent definition and a M.O.R. of 4.0 K.S.I., a C.T.E. of 56.0, and a translucency of 0.

During the forming process, the crucible retained its structural integrity, and formed an effective seal with the mold. Because the material used was a glass, the resulting dental restoration was not heat treated.

Example 16

A glass-ceramic dental composition was prepared and heat treated in accordance with this invention. The composition of the glass-ceramic material is in accordance with composition #8 of Table IV.

After melting, test samples were prepared in accordance with the procedure described above. The resulting test samples had a M.O.R. of 30 K.S.I., a C.T.E. of 157, a translucency of 40, and a softening temperature of 925° C.

The test samples cracked during heat treating, therefore, the composition was deemed to be unsuitable as a material for use in preparation of dental restoration. Accordingly, further tests were not carried out and a dental restoration was not formed.

Example 17

A glass-ceramic dental composition was prepared and heat treated in accordance with this invention. The composition of the glass-ceramic material is in accordance with composition #9 of Table IV.

After melting, test samples were prepared in accordance with the procedure described above. The resulting test samples had a M.O.R. of 24 K.S.I., a C.T.E. of 145, and a softening temperature of 975° C.

Because the test samples had a M.O.R. of only 24, and the glass-ceramic was hard to melt and form, the composition was deemed to be unsuitable as a material for use in preparation of dental restorations. Accordingly, further tests were not carried out and a dental restoration was not formed.

Example 18

A glass-ceramic dental composition was prepared and heat treated in accordance with this invention. The composition of the glass-ceramic material is in accordance with composition #10 of Table IV.

After melting, test samples were prepared in accordance with the procedure described above. The resulting test samples had a M.O.R. of 41.4 K.S.I., a C.T.E. of 129, a translucency of 2.5, and a softening temperature of 975° C.

Because the test samples had a C.T.E. of less than 130, the composition may not be suitable as a material for use in preparation of dental restorations. Accordingly, further tests were not carried out, and a dental restoration was not formed.

Example 19

A glass-ceramic dental composition was prepared and heat treated in accordance with this invention. The composition of the glass-ceramic material is in accordance with composition #11 of Table IV.

After melting, test samples were prepared in accordance with the procedure described above. The resulting test samples had a M.O.R. of 35 K.S.I., a C.T.E. of 80, a translucency of 3.5, and a softening temperature of 975° C.

Because the test samples had a C.T.E. of 80, the composition was deemed to be unsuitable as a material for use in the preparation of dental restorations. Accordingly, further tests were not carried out, and a dental restoration was not formed.

Example 20

A glass-ceramic dental composition was prepared and heat treated in accordance with this invention. The composition of the glass-ceramic material is in accordance with composition #12 of Table IV.

After melting, test samples were prepared in accordance with the procedure described above. The resulting test samples had a M.O.R. of 31 K.S.I., a C.T.E. of 127, and a translucency of 2.5.

Because the test samples had a C.T.E. of only 127, the composition may not be suitable as a material for use in preparation of dental restorations. Accordingly, further tests were not carried out, and a dental restoration was not formed.

Example 21

A glass-ceramic dental composition was prepared and heat treated in accordance with this invention. The composition of the glass-ceramic material is in accordance with composition #13 of Table IV.

After melting, test samples were prepared in accordance with the procedure described above. The resulting test samples had a M.O.R. of 32 K.S.I., a C.T.E. of 256, and a translucency of 5.0.

Because the test samples had a C.T.E. of 256, the composition was deemed to be unsuitable as a material for use in preparation of dental restorations. Accordingly, further tests were not carried out, and a dental restoration was not formed.

Example 22

A glass-ceramic dental composition was prepared and heat treated in accordance with this invention. The composition of the glass-ceramic material is in accordance with composition #14 of Table IV.

After melting, test samples were prepared in accordance with the procedure described above. The resulting test samples had a M.O.R. of 13 K.S.I., a C.T.E. of 126, and a translucency of 4.5.

Because the test samples had a low C.T.E. and a low M.O.R., the composition was deemed to be unsuitable as a material for use in preparation of dental restorations. Accordingly, further tests were not carried out, and a dental restoration was not formed.

Example 23

A glass-ceramic dental composition was prepared and elevated in accordance with this invention. The composition of the glass-ceramic material is in accordance with composition #15 of Table IV.

After melting, test samples were prepared in accordance with the procedure described above. The resulting test samples had a translucency of 5.0.

Because the test samples turned opaque during heat treating, the composition was deemed to be unsuitable as a material for use in preparation of dental restorations. Accordingly, further tests were not carried out, and a dental restoration was not formed.

Example 24

A glass-ceramic dental restoration was prepared in accordance with the following procedure. A mold was prepared in accordance with procedure described above.

By use of slip casting techniques, a crucible was prepared in accordance with the procedure and composition described above in connection with Example 6. A glass button weighing 6 grams was then placed in the crucible and preheated to a temperature of 650° C.

The composition of the glass-ceramic material used is in accordance with composition #16 of Table IV.

The preheated crucible and glass-ceramic material were then placed in an apparatus which is similar to that shown in FIG. 7, and heated to a temperature of 1425° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition, and a M.O.R. of 35 K.S.I., a C.T.E. of 148, a translucency of 3.5, and a softening temperature of 950° C.

During the forming process, the crucible retained its structural integrity and formed an effective seal with the mold. Further, during the heating process, the finished dental restoration retained its structural integrity and did not slump or deform.

The investment material utilized was Whipmix GIJM 2-23-94; as described herein above. The investment material had an expansion rate of about 3 percent. As a result of this expansion rate, the resulting dental restoration had excellent fit.

Example 25

A glass-ceramic dental restoration was prepared in accordance with the following procedure. A mold was prepared in accordance with procedure described above.

By use of slip casting techniques, a crucible was prepared in accordance with the procedure and composition described above in connection with Example 6. A glass button weighing 6 grams was then placed in the crucible and preheated to a temperature of 650° C.

The composition of the glass-ceramic material used is in accordance with composition #17 of Table IV.

The preheated crucible and glass-ceramic material were then placed in an apparatus which is similar to that shown in FIG. 7, and heated to a temperature of 1425° C. for a period of 10 minutes. The ram was then actuated, and the crucible was brought into contact with the mold in accordance with the general procedure as is illustrated in FIGS. 3 through 6.

The dental restoration was then heat treated in the investment.

The resulting test samples and dental restoration had excellent definition, and a M.O.R. of 40 K.S.I., a C.T.E. of 138, a translucency of 3.5, and a softening temperature of 950° C.

During the forming process, the crucible retained its structural integrity and formed an effective seal with the mold. Further, during the heating process, the finished dental restoration retained its structural integrity and did not slump or deform.

The investment material utilized was Thermovest, and after heat treating, was removed and the resulting dental restoration had excellent fit.

Example 26

A glass-ceramic dental restoration was prepared in accordance with the following procedure. A mold was prepared in accordance with procedure described above.

By use of slip casting techniques, a crucible was prepared in accordance with the procedure and composition described above in connection with Example 6. A glass button weighing 6 grams was then placed in the crucible.

The composition of the glass-ceramic material used is in accordance with composition #18 of Table IV.

The crucible and glass-ceramic material were then placed in an apparatus which is similar to that shown in FIGS. 7a and 7b, and heated to a temperature of 1425° C. for a period of 10 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition, and a M.O.R. of 47 K.S.I., a translucency of 4.0, and a softening temperature of 950° C.

During the forming process, the crucible retained its structural integrity and formed an effective seal with the mold. Further, during the heating process, the finished dental restoration retained its structural integrity and did not slump or deform.

The investment material utilized was Whipmix GIJM 2-23-94; as described herein above. The investment material had an expansion rate of about 3 percent. As a result of this expansion rate, the resulting dental restoration had excellent fit.

Example 27

A glass-ceramic dental restoration was prepared in accordance with the following procedure. A mold was prepared in accordance with procedure described above.

By use of slip casting techniques, a crucible was prepared in accordance with the procedure and composition described above in connection with Example 6. A glass button weighing 6 grams was then placed in the crucible and not preheated.

The composition of the glass-ceramic material used is in accordance with composition #19 of Table IV.

The crucible and glass-ceramic material were then placed in an apparatus which is similar to that shown in FIGS. 7a and 7b, and heated to a temperature of 1425° C. for a period of 5 minutes. The ram was then actuated, and the crucible was brought into contact with the mold in accordance with the general procedure as is illustrated in FIGS. 3 through 6.

The dental restoration was then removed from the investment material, cut apart from the sprue, and heat treated.

The resulting test samples and dental restoration had excellent definition, and a M.O.R. of 52 K.S.I., a translucency of 3.5, and a softening temperature of 950° C.

During the forming process, the crucible retained its structural integrity and formed an effective seal with the mold. Further, during the heating process, the finished dental restoration retained its structural integrity and did not slump or deform.

The investment material utilized was Whipmix GIJM 2-23-94; as described herein above. The investment material had an expansion rate of about 3 percent. As a result of this expansion rate, the resulting dental restoration had excellent fit.

Examples 26 and 27 represent the preferred process and glass-ceramic composition in accordance with this invention. As is mentioned, the resulting dental restorations of these examples were heat treated. The heat treating procedure used for examples 26 and 27 is per Table VIII.

TABLE VIII

| Heat Dental Restoration to | 450° C. at furnace rate |
| Ramp or Soak at | 450° to 550° C. for 6 hrs. |
| Ramp at | 550°–850° C. for 2 hrs. |
| Hold at | 850° C. for 45 minutes |
| Ramp at | 850°–900° C. at furnace rate |
| Soak at | 900° C. for 15 minutes |
| Cool to | Room Temperature |

After heat treating the dental restorations of examples 26 and 27, they were further finished by altering the shape and shade with a high fusing porcelain sold under the trademark CERAMCO II, and a low fusing porcelain sold under the trademark FINAL TOUCH. Both of the high and low fusing porcelains fired and adhered well. Likewise, both porcelains had thermal expansions which were compatible with the glass-ceramics from which the dental restorations were formed.

The CERAMCO II and FINAL TOUCH porcelains as used herein are manufactured and sold by Ceramco, Inc., of Six Teri Lane, Burlington, N.J.

Relative to the dental restorations as were produced in accordance with examples 26 and 27 above, it should be noted that these restorations were exceptionally strong in that they had M.O.R. ratings of about 50 K.S.I.

It should be noted that the M.O.R. ratings of examples 26 and 27 do not correlate with the M.O.R. ratings as are specified relative to the other examples, in that a different test protocol was use for measuring the M.O.R. of examples 26 and 27. The M.O.R. for examples 26 and 27 were tested on a Lloyd Instrument Type No. TG-18, as manufactured by John Chatillon & Sons, Inc., of Greensboro, N.C. These measurements were made in accordance with I.S.O. test no. 6872, using cylindrical bars of 0.125" diameter with a 1" span, 3 point bending with a cross head speed of 1 mm per minute.

In contrast, the M.O.R. measurements of the other examples were made on a piece of equipment which was manufactured by the Applicant. This piece of equipment has characteristics which are similar to those of the above-described Lloyd Instrument Type No. TG-18, and used the same test bars. Generally, it could be said that the M.O.R. rating of those examples other than examples 26 and 27 appear to be low.

For a correlation between the M.O.R. test protocol of examples 26 and 27, and the test protocol of the other examples, Table IX should be referred to.

TABLE IX

| Example No. | Reported M.O.R. As Per Test Used For Examples 1–25 | M.O.R. as Per I.S.O. Test No. 6872 |
| --- | --- | --- |
| 26 | 42 | 47 |
| 27 | 45 | 52 |

Example 28

A glass-ceramic dental restoration was prepared in accordance with the following procedure. A mold was prepared in accordance with the procedure described above.

By use of slip casting techniques, a crucible was prepared in accordance with the procedure and composition described above in connection with example 6. A glass button weighing 6 grams was then placed in the crucible and preheated to a temperature of 650° C.

The composition of the glass-ceramic material used is in accordance with composition #10 of Table IV.

The preheated crucible and glass-ceramic material was then placed in an apparatus which is similar to that shown in FIG. 7, and heated to a temperature of 1425° C. for a period of 10 minutes. The ram was then actuated, the crucible was brought into contact with the mold in accordance with the general procedure as is illustrated in FIGS. 3 through 6.

The dental restoration was then heat treated.

The resulting test samples and dental restoration had excellent definition, and a C.T.E. of 111, a translucency of 3.5, and a softening temperature of 850° C.

During the forming process, the crucible retained its structural integrity and formed an effective seal with the mold. Further, during the heat treating process, the finished dental restoration retained its structural integrity and did not slump or deform.

Example 29

A glass-ceramic dental restoration was prepared in accordance with the following procedure. A mold was prepared in accordance with the procedure described above.

The composition of the glass-ceramic material used is in accordance with composition 21 of Table IVb.

The glass-ceramic button was placed in an AUTO-PRESS™ Plus press as sold by Jeneric/Pentron of Wallingford, Conn., and preheated to a temperature of 850° C.–950° C. for a period of 10 minutes. The ram was then actuated, and the button was then pressed into the mold.

The dental restoration was then removed from the investment material, cut apart from the sprue, and made ready for applying dental porcelains.

The glass-ceramic material as used in this example had a C.T.E. (25°–500° C.), $10.3\pm0.5\times10^{-6}$, and a glass transition T-re° C. of 500±10.

Example 30

A glass-ceramic dental restoration was prepared in accordance with the following procedure. A mold was prepared in accordance with the procedure described above.

The composition of the glass-ceramic material used is in accordance with composition #22 of Table IVb.

The glass-ceramic button was placed in an AUTO-PRESS™ Plus press as sold by Jeneric/Pentron of Wallingford, Conn., and preheated to a temperature of 850° C.–950° C. for a period of 10 minutes. The ram was then actuated, and the button was then pressed into the mold.

The dental restoration was then removed from the investment material, cut apart from the sprue, and made ready for applying dental porcelains.

The glass-ceramic material as used in this example had a C.T.E. (25°–500° C.), $10.6\pm0.5\times10^{-6}$, and a glass transition T-re° C. of 500±10.

Example 31

A glass-ceramic dental restoration was prepared in accordance with the following procedure. A mold was prepared in accordance with the procedure described above.

The composition of the glass-ceramic material used is in accordance with composition #23 of Table IVb.

The glass-ceramic button was placed in an AUTO-PRESS™ Plus press as sold by Jeneric/Pentron of Wallingford, Conn., and preheated to a temperature of 850° C.–950° C. for a period of 10 minutes. The ram was then actuated, and the button was then pressed into the mold.

The dental restoration was then removed from the investment material, and cut apart from the sprue.

The glass-ceramic material as used in this example had a C.T.E. (25°–500° C.), $10.4\pm0.5\times10^{-6}$, and a glass transition T-re° C. of 500±10, a 3 point bend strength per I.S.O. 6872 MPa of 315±24, a solubility per I.S.O. 9693 ng/cm° of 60, and a solubility per I.S.O. 6872 ng/cm° of 73.

Example 32

A glass-ceramic dental restoration was prepared in accordance with the following procedure. A mold was prepared in accordance with the procedure described above.

The composition of the glass-ceramic material used is in accordance with composition #24 of Table IVb.

The glass-ceramic button was placed in an AUTO-PRESS™ Plus press as sold by Jeneric/Pentron of Wallingford, Conn., and preheated to a temperature of about 930° C. for a period of 10 minutes. The ram was then actuated, and the button was then pressed into the mold.

The dental restoration was then removed from the investment material, and cut apart from the sprue.

The glass-ceramic material as used in this example had a C.T.E. (25°–500° C.), $10.3\pm0.5\times10^{-6}$, and a glass transition T-re° C. of 500±10, a 3 point bend strength per I.S.O. 6872 MPa of 300±30, a solubility per I.S.O. 9693 ng/cm° of less than 100, and a solubility per I.S.O. 6872 ng/cm° of less than 100.

It should be understood that the invention is not limited to the embodiment shown and described in FIGS. 1 through 10, and examples 1 through 32, since the process and composition parameters can be varied, and the configuration of the apparatus can be altered without departing from the scope of the invention.

The above description and drawings are illustrative only, since modifications could be made without departing from the present invention, the scope of which is to be limited only by the following claims.

What is claimed is:

1. A dental restoration which is formed from a glass ceramic material, which does not deform during heat treating, comprising the following composition (by weight percent);

| | |
|---|---|
| $Li_2O$ | 8–15 |
| $Al_2O_3$ | 1.5–5.0 |
| $SiO_2$ | 60–80 |
| $P_2O_5$ | 1.5–5.0 |
| Coloring Oxides | Up to 5 |
| Fluorescing Agents | Up to 5 |
| Pigments + Opacifiers | |
| Glass Modifiers | Balance. | and wherein the glass ceramic material has a softening temperature of at least 850° C.

2. A dental restoration which is formed from a glass-ceramic material, which does not deform during heat treating, comprising the following composition (by weight percent;

and wherein the glass ceramic materials has a softening temperature of at least 850° C.

3. A dental restoration which is formed from a glass-ceramic material, which does not deform heat treating, comprising the following composition (by weight percent);

and wherein the glass ceramic material has a softening temperature of at least 850° C.

4. A dental restoration which if formed from a glass-ceramic material, which does not deform during heat treating, comprising the following composition (by weight percent);
and wherein the glass ceramic material has a softening temperature of at least 850° C.

5. A dental restoration which is formed from a glass-ceramic material, which does not deform during heat treating, comprising the following composition (by weight percent);
and wherein the glass ceramic material has a softening temperature of at least 850° C.

6. A dental restoration which is formed from a glass-ceramic material, which does not deform during heat treating, comprising the following composition by (weight percent);
and wherein the glass ceramic material has a softening temperature of at least 850° C.

7. A dental restoration which is formed from a glass-ceramic material, which does not deform during heat treating, comprising the following composition (by weight percent);
and wherein the glass ceramic material has a softening temperature of at least 850° C.

8. The dental restoration of claim 1, wherein said dental restoration is further altered by applying one or more layer(s) of a porcelain material to said dental restoration, and fusing said porcelain layer(s);
wherein the C.T.E. of said porcelain material is slightly more or less than the C.T.E. of the glass ceramic material.

9. The dental restoration of claim 2, wherein said dental restoration is further altered by applying one or more layer(s) of a porcelain material to said dental restoration, and fusing said porcelain layer(s);
wherein the C.T.E. of said porcelain material is slightly more or less than the C.T.E. of the glass ceramic material.

10. The dental restoration of claim 3 wherein said dental restoration is further altered by applying one or more layer(s) of a porcelain material to said dental restoration, and fusing said porcelain layer(s);
wherein the C.T.E. of said porcelain material is slightly more or less than the C.T.E. of the glass ceramic material.

11. The dental restoration of claim 4, wherein said dental restoration is further altered by applying one or more layer(s) of a porcelain material to said dental restoration, and fusing said porcelain layer(s);
wherein the C.T.E. of said porcelain material is slightly more or less than the C.T.E. of the glass ceramic material.

12. The dental restoration of claim 5 wherein said dental restoration is further altered by applying one or more layer(s) of a porcelain material to said dental restoration, and fusing said porcelain layer(s)
wherein the C.T.E. of said porcelain material is slightly more or less than the C.T.E. of the glass ceramic material.

13. The dental restoration of claim 6, wherein said dental restoration is further altered by applying one or more layer(s) of a porcelain material to said dental restoration, and fusing said porcelain layer(s);
wherein the C.T.E. of said porcelain material is slightly more or less than the C.T.E. of the glass ceramic material.

14. The dental restoration of claim 7 wherein said dental restoration is further altered by applying one or more layer(s) of a porcelain material to said dental restoration, and fusing said porcelain layer(s);
wherein the C.T.E. of said porcelain material is slightly more or less than the glass ceramic material.

* * * * *

UNITED STATES PATENT AND TRADEMARK OFFICE
CERTIFICATE OF CORRECTION

PATENT NO.    : 6,485,849 B2
DATED         : November 26, 2002
INVENTOR(S)   : Richard W. Petticrew It is certified that error appears in the above-identified patent and that said Letters Patent is hereby corrected as shown below:

Column 11,
After line 54, add the following table.

TABLE IV

|        | 1    | 2    | 3    | 4    | 5    | 6    | 7    | 8    | 9    | 10   | 11   | 12   | 13   | 14   | 15   | 16   | 17   | 18   | 19   | 20   |
|--------|------|------|------|------|------|------|------|------|------|------|------|------|------|------|------|------|------|------|------|------|
| $SiO_2$ | 81.0 | 84.0 | 84.0 | 83.0 | 82.0 | 84.0 | 81.0 | 83.0 | 83.0 | 81.5 | 80.0 | 86.0 | 84.0 | 81.0 | 82.0 | 82.0 | 81.0 | 78.5 | 80.6 | 72.5 |
| $Al_2O_3$ | 3.5 | 3.0 | 3.0 | 3.0 | 4.0 | 3.3 | 3.3 | 3.5 | 3.5 | 3.0 | 6.0 | 1.5 |  | 3.0 | 3.3 | 3.5 | 3.0 | 2.5 | 2.3 | 2.5 |
| $Li_2O$ | 11.0 | 10.5 | 10.5 | 10.5 | 10.5 | 10.0 | 11.0 | 9.0 | 8.0 | 12.0 | 10.5 | 10.5 | 11.0 | 11.0 | 10.0 | 10.0 | 11.0 | 10.5 | 12.5 | 10.5 |
| $P_2O_5$ | 3.0 | 2.0 | 2.0 | 2.0 | 2.0 | 1.5 | 1.5 | 3.0 | 3.0 | 2.0 | 2.0 | 2.0 | 3.0 | 1.0 | 1.5 | 2.2 | 3.0 | 2.0 | 2.0 | 2.0 |
| $ZrO_2$ | 1.0 | 0.5 |  | 0.5 | 0.5 |  | 2.0 |  |  | 0.5 | 0.5 |  | 1.0 | 2.0 |  | 2.0 | 1.0 | 0.5 | 1.0 | 0.5 |
| $TiO_2$ | 0.4 |  |  |  |  | 0.1 | 1.0 | 0.5 |  |  |  |  | 0.4 | 0.4 |  | 0.5 | 0.4 | 0.1 | 0.1 | 0.1 |
| CaO | 0.5 | 0.25 | 0.25 | 0.25 | 0.25 | 0.25 | 0.25 | 0.25 | 0.25 | 0.25 | 0.25 |  | 0.50 | 0.50 |  | 0.25 | 0.50 | 0.35 | 0.35 | 0.42 |
| $MnO_2$ |  | 0.5 | 0.5 | 0.5 | 0.5 |  |  |  |  |  |  |  |  |  |  |  |  |  |  | 0.75 |
| $NiO_2$ |  |  |  |  |  | 0.06 |  |  |  |  |  | 0.5 |  |  |  |  |  | 0.02 | 0.02 |  |
| $K_2O$ |  |  | 0.5 | 0.5 | 0.5 | 1.0 |  |  | 1.0 | 0.5 | 0.5 |  |  |  |  |  |  | 0.5 | 0.5 |  |
| $Na_2O$ | 0.5 |  |  |  |  | 0.2 | 0.2 | 0.5 | 0.5 |  |  |  |  |  | 0.2 | 3.0 |  |  |  |  |
| $Fe_2O_3$ |  |  |  |  |  | 0.09 | 0.09 | 0.09 |  |  |  |  |  |  |  | 0.09 |  |  |  |  |
| BaO |  |  |  |  |  |  |  |  |  |  |  |  |  |  | 3.0 |  |  | 3.0 | 0.5 | 9.0 |
| MgO |  |  |  |  |  |  |  | 1.0 |  |  |  |  |  |  |  |  |  |  |  |  |
| CaO |  |  |  |  |  |  |  |  | 1.0 |  |  |  |  |  |  |  |  | 0.4 | 0.4 | 0.4 |

Column 30,
After line 62, add the following;

| | |
|---|---|
| $Li_2O$ | 8 - 15 |
| $Al_2O_3$ | 1.5 - 5.0 |
| $SiO_2$ | 60 - 80 |
| $P_2O_5$ | 1.5 - 5.0 |
| $Na_2O$ | Up to 2 |
| $K_2O$ | Up to 2 |
| $ZrO_2$ | Up to 3 |
| CaO | Up to 1 |
| $BaO+SrO+La_2O_3$ | Up to 12 |
| Coloring Oxides | Up to 5 |
| Fluorescing Agents +Pigments+Opacifiers | Up to 5 |

UNITED STATES PATENT AND TRADEMARK OFFICE
CERTIFICATE OF CORRECTION

PATENT NO. : 6,485,849 B2
DATED : November 26, 2002
INVENTOR(S) : Richard W. Petticrew It is certified that error appears in the above-identified patent and that said Letters Patent is hereby corrected as shown below:

Column 31,
After line 2, add the following;

| | |
|---|---|
| $Li_2O$ | 14 – 15 |
| $Al_2O_3$ | 4.5 – 5.0 |
| $SiO_2$ | 67 – 71 |
| $Na_2O$ | 1 – 2 |
| $K_2O$ | 1.5 – 3.5 |
| $P_2O_5$ | 3 – 4 |
| $B_2O_3$ | 0 – 2 |
| CaO | 0 – 1.25 |
| BaO | 1.25 – 3 |
| $Tb_4O_7$ | 0 – 1 |
| $CeO_2$ | 0 – 1 |
| CaO | 0 – 1.25 |

After line 6, add the following;

| | |
|---|---|
| $SiO_2$ | About 70.6 |
| $Al_2O_3$ | About 4.8 |
| $Li_2O$ | About 14.7 |
| $P_2O_5$ | About 3.6 |
| CaO | About 0.5 |
| $K_2O$ | About 2.0 |
| $Na_2O$ | About 1.4 |
| BaO | About 1.4 |

UNITED STATES PATENT AND TRADEMARK OFFICE
CERTIFICATE OF CORRECTION

PATENT NO. : 6,485,849 B2
DATED : November 26, 2002
INVENTOR(S) : Richard W. Petticrew It is certified that error appears in the above-identified patent and that said Letters Patent is hereby corrected as shown below:

Column 31 cont'd,
After line 12, add the following;

| | |
|---|---|
| $SiO_2$ | About 68.7 |
| $Al_2O_3$ | About 4.8 |
| $Li_2O$ | About 14.4 |
| $P_2O_5$ | About 3.3 |
| CaO | About 1.0 |
| $K_2O$ | About 2.0 |
| $Na_2O$ | About 1.5 |
| BaO | About 2.8 |
| $Tb_4O_7$ | About 0.7 |
| $CeO_2$ | About 0.7 |

After line 18, add the following;

| | |
|---|---|
| $SiO_2$ | About 68.8 |
| $Al_2O_3$ | About 4.8 |
| $Li_2O$ | About 14.5 |
| $P_2O_5$ | About 3.3 |
| CaO | About 1.0 |
| $K_2O$ | About 2.0 |
| $Na_2O$ | About 1.5 |
| BaO | About 2.8 |
| $B_2O_3$ | About 1.3 |

UNITED STATES PATENT AND TRADEMARK OFFICE
CERTIFICATE OF CORRECTION

PATENT NO.    : 6,485,849 B2
DATED         : November 26, 2002
INVENTOR(S)   : Richard W. Petticrew It is certified that error appears in the above-identified patent and that said Letters Patent is hereby corrected as shown below:

Column 31 cont'd,
After line 4, add the following:

| | |
|---|---|
| $SiO_2$ | About 68.8 |
| $Al_2O_3$ | About 4.8 |
| $Li_2O$ | About 14.4 |
| $P_2O_5$ | About 3.3 |
| CaO | About 1.0 |
| $K_2O$ | About 2.0 |
| $Na_2O$ | About 1.4 |
| BaO | About 2.8 |

Signed and Sealed this

Twenty-ninth Day of April, 2003

JAMES E. ROGAN
*Director of the United States Patent and Trademark Office*